(12) United States Patent
Langley

(10) Patent No.: US 9,117,040 B2
(45) Date of Patent: Aug. 25, 2015

(54) INDUCED FIELD DETERMINATION USING DIFFUSE FIELD RECIPROCITY

(76) Inventor: Robin Stewart Langley, Cambridge (GB)

( * ) Notice: Subject to any disclaimer, the term of this patent is extended or adjusted under 35 U.S.C. 154(b) by 965 days.

(21) Appl. No.: 13/227,330

(22) Filed: Sep. 7, 2011

(65) Prior Publication Data

US 2012/0265464 A1    Oct. 18, 2012

Related U.S. Application Data

(60) Provisional application No. 61/474,367, filed on Apr. 12, 2011.

(51) Int. Cl.
*G06F 7/60* (2006.01)
*G06F 17/10* (2006.01)
*G06F 17/50* (2006.01)
*G01V 3/165* (2006.01)

(52) U.S. Cl.
CPC ............ *G06F 17/5018* (2013.01); *G01V 3/165* (2013.01); *G01V 2210/6163* (2013.01)

(58) Field of Classification Search
CPC ......... G01V 3/081; G01V 3/165; G01V 3/17; G01V 3/30; G01V 2210/6163; G01S 13/78; G01S 1/70; G01S 17/46; G06F 17/5018; G06F 17/5004
USPC ................ 703/2, 5; 367/455, 342, 77; 702/65
See application file for complete search history.

(56) References Cited

U.S. PATENT DOCUMENTS

| 5,189,366 A | 2/1993 | Mayo |
| 5,751,600 A | 5/1998 | Ochi et al. |
| 2003/0019291 A1 | 1/2003 | Pchelnikov et al. |
| 2006/0279273 A1 | 12/2006 | Kazama |

OTHER PUBLICATIONS

Langley, Robin S., "A Reciprocity Approach for Computing the Response of Wiring Systems to Diffuse Electromagnetic Fields", Nov. 17, 2010, IEEE Transactions on Electromagnetic Compatibility, vol. 52, No. 4, IEEE.*
Langley, R. S., "On the Diffuse Field Reciprocity Relationship and Vibrational Energy Variance in a Random Subsystem at High Frequencies", Feb. 2007, Journal of Acoustic Society of America, Acoustic Society of America.*

(Continued)

*Primary Examiner* — Kamini S Shah
*Assistant Examiner* — Cedric D Johnson
(74) *Attorney, Agent, or Firm* — Bryan Cave LLP

(57) ABSTRACT

Methods and systems are provided for determining the surface electromagnetic impedance of a conductive element and applying the diffuse field reciprocity principle using that surface electromagnetic impedance to determine electric fields induced in the conductive element. An exemplary method involves determining a surface electromagnetic impedance matrix for the conductive element based on its physical dimensions and an excitation frequency for an incident electromagnetic wavefield, applying diffuse field reciprocity to determine a metric indicative of an induced field based on the surface electromagnetic impedance matrix and an energy metric for the incident electromagnetic wavefield, and displaying a graphical representation of the metric on a display device.

16 Claims, 16 Drawing Sheets

(56) References Cited

OTHER PUBLICATIONS

Shorter, P.J. et al., "On the Reciprocity Relationship Between Direct Field Radiation and Diffuse Reverberant Loading", Jan. 2005, Journal of Acoustic Society of America, Acoustic Society of America.*

Andersen, J. Bach et al., "Room Electromagnetics", Apr. 2007, IEEE Antennas and Propagation Magazine, vol. 49, No. 2, IEEE.*

Ishimaru, Akira et al., "Sommerfeld and Zenneck Wave Propagation for a Finely Conducting One-Dimensional Rough Surface", Sep. 2000, IEEE Transactions on Antennas and Propagation, vol. 48 No. 9, IEEE.*

International Search Report and Written Opinion for PCT/US2014/043482, 14 pages, Oct. 10, 2014.

* cited by examiner

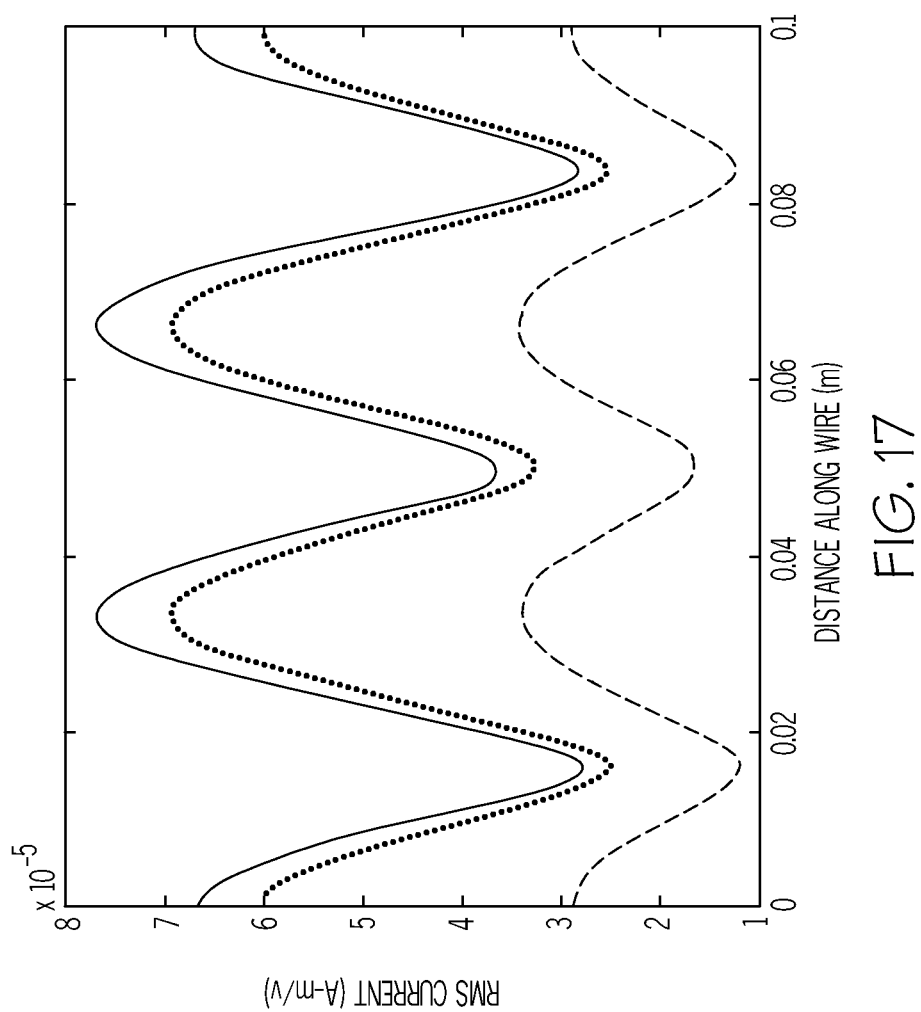

INDUCED FIELD DETERMINATION USING DIFFUSE FIELD RECIPROCITY

CROSS-REFERENCE TO RELATED APPLICATION(S)

This application claims the benefit of U.S. provisional patent application Ser. No. 61/474,367, filed Apr. 12, 2011, the entire content of which is incorporated by reference herein.

TECHNICAL FIELD

The subject matter described herein relates generally to determining induced electromagnetic fields, and more particularly, embodiments of the subject matter relate to calculating induced electromagnetic fields using diffuse field reciprocity principles.

BACKGROUND

Electromagnetic interference is a common problem that designers of electrical circuits, devices, and systems are concerned with due to the potential of electromagnetic interference disrupting normal operation of such electrical circuits, devices, and systems. In practice, there are numerous potential sources of electromagnetic interference. For example, a designer of an electrical system for an automotive vehicle must be concerned with various potential sources of electromagnetic interference (e.g., cellular base stations, wireless networks, cellular devices, wireless devices, Bluetooth devices, other vehicle electrical systems, and the like) that may be encountered during operation of the vehicle. Thus, there are many situations in which potentially harmful currents could be induced in vehicle wiring systems by electromagnetic fields. Accordingly, it is desirable to calculate or otherwise estimate the response of the vehicle wiring system to electromagnetic interference (e.g., the induced currents, voltages, and the like within the wires) and analyze the potential effects at the design stage to help ensure the integrity of the system.

In many cases the frequency of the electromagnetic interference is relatively high, in the sense that the electromagnetic wavelength is short in comparison to the dimensions of the vehicle interior. For example, a typical mobile phone transmitter may produce excitation at around 2 GHz, leading to a wavelength of 15 cm, meaning that the electromagnetic field will have a spatially complex distribution within a typical automotive vehicle interior. Traditionally, to estimate the response of the vehicle wiring systems and/or electronics, the detailed spatial distribution of the electromagnetic field is determined numerically by solving Maxwell's equations within the vehicle, although very many grid points will be required by either the finite element method or the finite difference method. Additionally, the computation of the response of the vehicle wiring systems and/or electronics to the electromagnetic field requires a model of the vehicle wiring systems and/or electronics to be coupled to the model of the electromagnetic field. While there are numerous existing modeling methods, calculating the response to the electromagnetic interference using these approaches requires a significant amount of computation time and resources.

BRIEF SUMMARY

As described in greater detail below, the relationship between an electromagnetic impedance at a surface of a conductive element and the excitation arising from an electromagnetic field incident on that surface, alternatively referred to herein as the diffuse field reciprocity principle (or diffuse field reciprocity relation), is utilized to determine one or more metrics (e.g., current, voltage, or the like) that are indicative of the electric and/or magnetic fields induced in the conductive element by the incident electromagnetic field. In an exemplary embodiment, the surface electromagnetic impedance of the conductive element is determined in wavenumber space and transformed to the physical domain using the physical dimensions of the conductive element and the excitation frequency of the incident electromagnetic field, which are provided by a user. Additionally, in one or more embodiments, the surface electromagnetic impedance is modified to impose boundary conditions at the termination points (or end points) of the conductive element. After the surface electromagnetic impedance is obtained, the diffuse field reciprocity principle is applied by multiplying the surface electromagnetic impedance by the energy density of the incident electromagnetic field to obtain a metric indicative of the induced magnetic field at the surface of the conductive element, which corresponds to the induced current in the conductive element. Additionally, in exemplary embodiments, a voltage recovery matrix for the conductive element is determined that allows the induced voltages within the conductive element to be calculated using the metric indicative of the induced magnetic field that was obtained by applying the diffuse field reciprocity principle. The various outputs indicative of the induced electromagnetic field in the conductive element may then be provided to the user, for example, by displaying graphical representations of the induced current and induced voltage on a display device.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 17 is a graph of induced current with respect to distance along a conductive element in response to a diffuse field excitation for a two wire transmission line with a short circuit at each end.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration," and any implementation described herein as exemplary is not necessarily to be construed as preferred or advantageous over other implementations. Furthermore, there is no intention to be bound by any expressed or implied theory presented in the preceding technical field, background, or the following detailed description.

Figure 1:
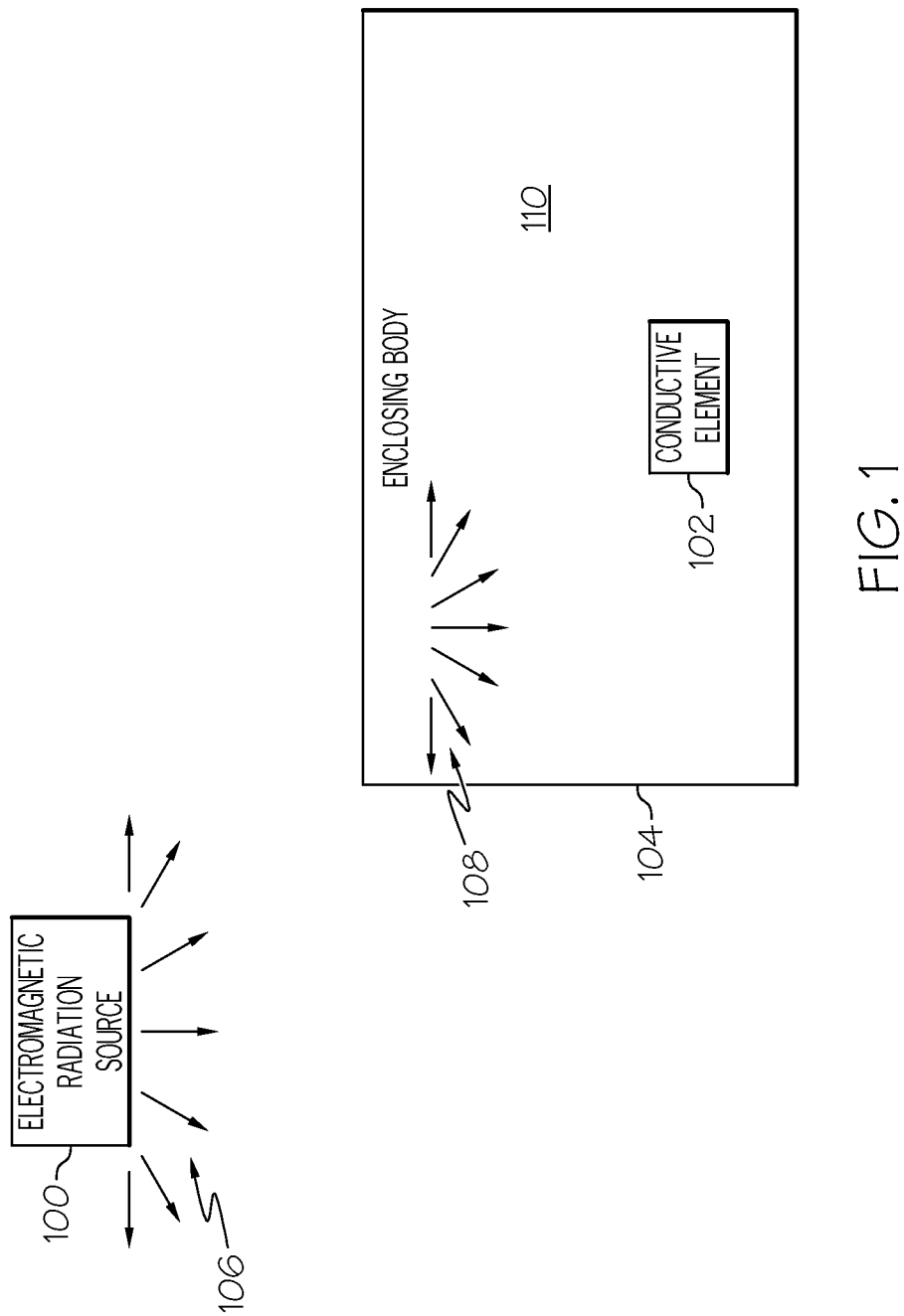
FIG. 1 is a block diagram of an exemplary operative environment for illustrating the application of the subject matter described herein.

FIG. 1 depicts a simplified representation of an exemplary operative environment having an electromagnetic radiation source 100 capable of inducing electromagnetic fields in a conductive element 102 within an enclosing body 104. In practice, the electromagnetic radiation source 100 may be any source of electromagnetic radiation, such as for example, cellular base stations, wireless networks, cellular devices, wireless devices, Bluetooth devices, or other radio frequency (RF) transmitting devices. Accordingly, the subject matter described herein is not intended to be limited to any particular type of electromagnetic radiation source or any particular excitation frequency for the emitted electromagnetic waves. Furthermore, although FIG. 1 depicts the electromagnetic radiation source 100 as being located outside the enclosing body 104, in practice, the electromagnetic radiation source 100 may be located within the enclosing body 104 (e.g., a cellular phone or Bluetooth device inside the passenger cabin of an automotive vehicle).

In the illustrated embodiment, the conductive element 102 represents any conductive element that is capable of having electromagnetic fields induced therein in response to electromagnetic radiation emitted by the electromagnetic radiation source 100. Depending on the embodiment, the conductive element 102 may be realized as one or more wires, cables, transmission lines, conductive traces, electrical components, electronic circuits, or any suitable combination thereof. Accordingly, the subject matter described herein is not intended to be limited to any particular type or number of conductive elements. However, for purposes of explanation, the conductive element 102 may be described herein as being comprised of one or more wires (alternatively referred to as transmission lines) in a vehicle wiring system in an automotive vehicle application. The enclosing body 104 generally represents any enclosure or housing capable of containing or otherwise substantially enclosing the conductive element 102 to provide a substantially finite dielectric medium 110 surrounding the conductive element 102. It should be understood that the subject matter described herein is not intended to be limited to any particular type of enclosing body and the conductive element 102 and/or dielectric medium 110 need not be perfectly enclosed (e.g., the enclosing body 104 need not be airtight or otherwise provide a continuous enclosure). For purposes of explanation, the enclosing body 104 may be described herein as an automotive vehicle.

As illustrated in FIG. 1, the electromagnetic wavefield (or waves) 106 emitted by the electromagnetic radiation source 100 induces or otherwise produces a corresponding electromagnetic wavefield 108 within the dielectric medium 110 confined by the vehicle body 104. As described in greater detail below, the electromagnetic wavefield 108 inside the vehicle body 104 can be approximated as an ideal diffuse wavefield, where there is an equal probability of electromagnetic waves propagating in all possible directions within the enclosing body 104, which can be exploited to provide a computationally efficient technique for predicting the response of the conductive element 102 (e.g., the induced currents and/or voltages) to the reverberating electromagnetic wavefield 108 within the vehicle body 104 using the diffuse field reciprocity principle. As described in greater detail below with reference to equations (1)-(18) and FIG. 6, the diffuse field reciprocity principle provides that the loading applied (e.g., the induced electric fields) by a random component (e.g., the electromagnetic wavefield 108 within the vehicle body 104) on a deterministic component (e.g., the conductive element 102) can be expressed in terms of the energy in the random component and the radiation properties of the deterministic component (i.e., the way in which the deterministic component would radiate into the random component, were the random component infinitely extended).

Figure 2:
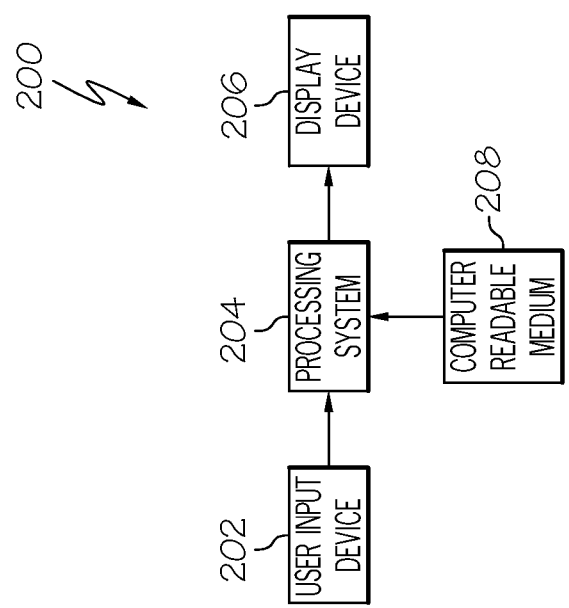
FIG. 2 is a block diagram of an exemplary computing system.

FIG. 2 depicts an exemplary embodiment of a computing system 200 capable of executing the processes, tasks, and functions described in greater detail below in the context of FIGS. 3-5. The illustrated computing system 200 includes, without limitation, a user input device 202, a processing system 204, an output device 206, and a computer-readable medium 208. It should be understood that FIG. 2 is a simplified representation of a computing system for purposes of explanation and is not intended to limit the scope of the subject matter in any way.

The user input device 202 generally represents the hardware and/or other components configured to provide a user interface with the computing system 200. Depending on the embodiment, the user input device 202 may be realize as a key pad, a keyboard, one or more button(s), a touch panel, a touchscreen, an audio input device (e.g., a microphone), or the like. The output device 206 generally represents the hardware and/or other components configured to provide output to the user from the computing system 200, as described in greater detail below. In an exemplary embodiment, the output device 206 is realized as an electronic display device configured to graphically display information and/or content under control of the processing system 204, as described in greater detail below.

Still referring to FIG. 2, the processing system 204 generally represents the hardware, software, firmware, processing logic, and/or other components of the computing system 200 coupled to the user input device 202 and the display device 206 to receive input from the user, utilize the input provided by the user to execute various functions and/or processing tasks, and provide an output to the user, as described in greater detail below. Depending on the embodiment, the processing system 204 may be implemented or realized with a computer, a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by processing system 204, or in any practical combination thereof. The computer-readable medium 208 may be realized as any non-transitory short or long term storage media capable of storing programming instructions or other data for execution by the processing system 204, including any sort of random access memory (RAM), read only memory (ROM), flash memory, registers, hard disks, removable disks, magnetic or optical mass storage, and/or the like. The computer-executable programming instructions, when read and executed by the processing system 204, cause the processing system 204 to execute one or more processes and perform the tasks, operations, and/or functions described in greater detail below in the context of FIGS. 3-5.

Referring now to FIGS. 1-2, in an exemplary embodiment, the processing system 204 executes the programming instructions stored or otherwise encoded on the computer-readable medium 208, which causes the processing system 204 to display one or more graphical user interface elements (e.g., text boxes or the like) on the display device 206 that are adapted to receive user inputs indicative of the physical dimensions and/or physical layout of the conductive element 102 and the energy density and excitation frequency of the electromagnetic wavefield incident on the conductive element 102 (i.e., electromagnetic wavefield 108). The processing system 204 may also display graphical user interface elements on the display device 206 that are adapted to receive user inputs indicative of the physical properties of the conductive element 102 and/or the dielectric medium 110, such as, for example, the permeability of the conductive element 102, the permittivity of the conductive element 102, the conductance of the conductive element 102, the permeability of the dielectric medium 110, the volume of the dielectric medium 110, and the like. Additionally, the processing system 204 may display graphical user interface elements on the display device 206 that are adapted to receive user inputs indicative of any boundary conditions (e.g., termination voltages and/or termination currents) to be applied to the conductive element 102. Subsequently, the user of the computing system 200 manipulates the user input device 202 to provide the physical dimensions and/or physical layout of the conductive element 102 and the energy density and excitation frequency of the incident electromagnetic wavefield 108, along with any other desired inputs, to the processing system 204.

After providing the desired input information, the user may manipulate the user input device 202 to select a graphical user interface element (e.g., a button or the like) that causes the processing system 204 to continue executing the programming instructions using the inputs received from the user. As described in greater detail below, the processing system 204 receives or otherwise obtains user inputs provided by the user and determines a surface electromagnetic impedance matrix for the conductive element 102 that corresponds to radiation from the surface of the conductive element 102 into an infinite dielectric medium and represents the relationship between the electric field and the magnetic field at the surface of the conductive element 102, while at the same time imposing any boundary conditions provided by the user. Additionally, in accordance with one or more embodiments, the processing system 204 utilized the boundary conditions provided by the user to determine a voltage recovery matrix for the conductive element 102. After determining the surface electromagnetic impedance matrix and voltage recovery matrix for the conductive element 102, the processing system 204 applies the diffuse field reciprocity principle by multiplying the surface electromagnetic impedance matrix for the conductive element 102 by the energy density for the incident electromagnetic wavefield 108 to obtain a metric indicative of the mean square of the induced magnetic field at the surface of the conductive element 102, which corresponds to the mean square induced current in the conductive element 102, as described in greater detail below. The term "mean square" as used herein should be understood as encompassing the ensemble average of a time averaged second order product, where the ensemble corresponds to different realizations of the random incident electromagnetic field, as well as the "cross-spectrum" when the variable of interest is a vector rather than a scalar. As described in greater detail below, the processing system 204 utilizes the mean square induced magnetic field and the voltage recovery matrix to determine the induced voltage in the conductive element 102. The processing system 204 then displays, on the display device, one or more graphical representations of the metrics indicative of the induced electric fields in the conductive element. For example, the processing system 204 may display a plot or graph of the mean square induced current (or a variant thereof) with respect to a position or distance along the conductive element 102, or a plot or graph of the induced voltage (or a variant thereof) with respect to a position or distance along the conductive element 102, as described in greater detail below in the context of FIGS. 8, 10, 12-15 and 17.

Figure 3:
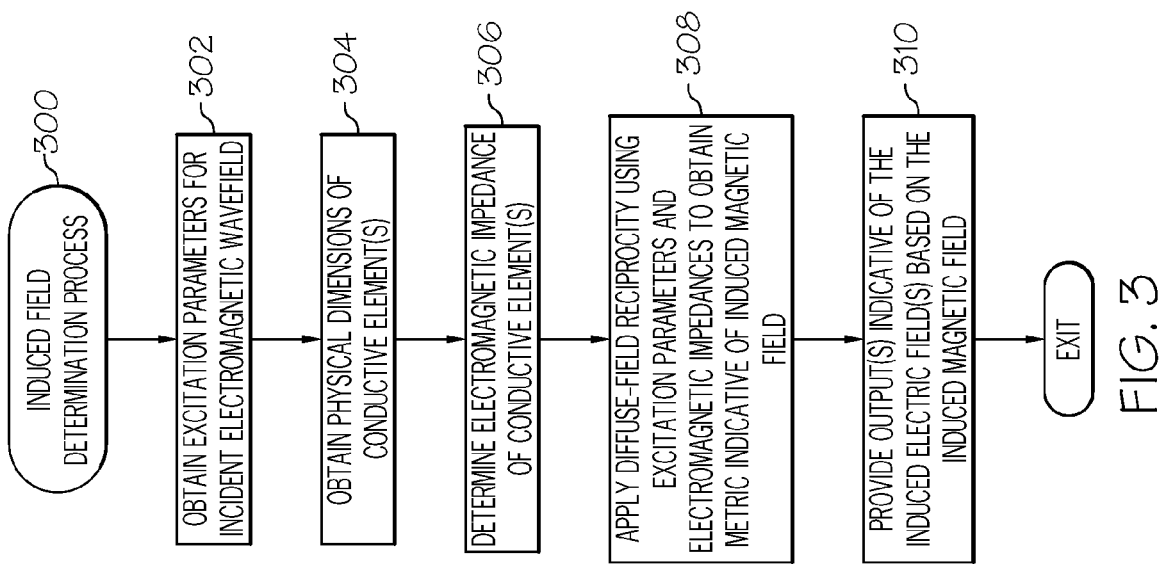
FIG. 3 is a flow diagram that illustrates an exemplary induced field determination process suitable for use with the computing system of FIG. 2.

FIG. 3 is a flow chart that illustrates an exemplary embodiment of an induced field determination process 300 suitable for calculating, determining, or otherwise estimating the induced electromagnetic fields, currents, and/or voltages induced by a diffuse electromagnetic wavefield (e.g., electromagnetic wavefield 108) in a conductive element (e.g., conductive element 102). The various tasks performed in connection with the illustrated process 300 may be performed by software, hardware, firmware, or any combination thereof. For illustrative purposes, the following description of illustrated processes may refer to elements mentioned above in connection with FIG. 1 and FIG. 2. It should be appreciated that the process 300 may include any number of additional or alternative tasks, the tasks need not be performed in the illustrated order and/or the tasks may be performed concurrently, and/or the process 300 may be incorporated into a more comprehensive procedure or process having additional functionality not described in detail herein. Moreover, one or more of the tasks shown and described in the context of FIG. 3 could be omitted from an embodiment of the respective process as long as the intended overall functionality remains intact.

In an exemplary embodiment, the process 300 begins by obtaining parameters for the electromagnetic wavefield incident to the conductive element(s) being analyzed (task 302). For example, as described above, a user provides (e.g., to processing system 204 via user input device 202) the electromagnetic energy density for the electromagnetic wavefield that is induced in the dielectric medium (e.g., electromagnetic wavefield 108) and incident on the conductive element(s) being analyzed (e.g., conductive element 102). As described in greater detail below, in accordance with one or more embodiments, the user provides the time averaged energy density (U) of the incident wavefield along with the excitation frequency ($\omega$) of the wavefield, which is utilized in conjunction with the permeability and volume of the dielectric medium (which may also be provided by the user, as described above) to determine the modal density (v) of electromagnetic modes in the dielectric medium surrounding the conductive element(s). The process 300 continues by obtaining the physical dimensions and/or layout of the conductive element(s) being analyzed (task 304). As described above, the process 300 receives of otherwise obtains from the user (e.g., via user input device 202) information that defines the physical dimensions (e.g., length, width, radius, and the like), shape, and/or structure of the conductive element(s) being analyzed. For multiple conductive elements, the user may also provide the distance (or spacing) between conductive elements. In this manner, the user defines the physical model of the conductive element(s) being analyzed.

Still referring to FIG. 3, after obtaining the physical dimensions of the conductive element(s), the process 300 continues by determining the surface electromagnetic impedance of the conductive element(s) based on the physical dimensions of the conductive element(s) and the excitation frequency for the incident wavefield (task 306). As described above and in greater detail below in the context of FIG. 4, the process 300 determines an impedance matrix that is associated with electromagnetic radiation from the surface of the conductive element(s) into an infinite dielectric medium free of signal reflections. In this regard, the surface electromagnetic impedance matrix is representative of the relationship between the electric field and the magnetic field at the surface of the conductive element(s). In an exemplary embodiment, the electromagnetic impedance matrix for the conductive element(s) are determined in wavenumber space (or frequency domain) based on exact solutions to Maxwell's equations in cylindrical coordinates, as provide by equations (34)-(35) and (53)-(55) described below, using the input excitation frequency obtained from the user, as described in greater detail below with reference to with reference to equations (24)-(40). The electromagnetic impedance matrix is then transformed into the physical domain from wavenumber space based on the information pertaining to the physical dimensions of the conductive element(s), as described in greater detail below with reference to equations (73)-(78). In one or more embodiments, the transformation from wavenumber space is accomplished using basis functions that are based on the sinc function. Additionally, in exemplary embodiments, boundary conditions (which may be specified by the user) are imposed when determining the electromagnetic impedance matrix for conductive element(s) of finite length, as described in greater detail below with reference to equation (86).

After determining the surface electromagnetic impedance matrix for the conductive element(s), the process 300 continues by applying the diffuse field reciprocity principle using the surface electromagnetic impedance matrix and the excitation parameters to obtain a metric indicative of the magnetic field induced in the conductive element(s) by the incident electromagnetic wavefield (task 308). After applying diffuse field reciprocity to obtain a metric indicative of the induced magnetic field, the process 300 determines one or more metrics indicative of the induced electric field(s) (e.g., an induced current metric, an induced voltage metric, or the like) in the conductive element (s) by the incident electromagnetic wavefield based on the induced magnetic field and provides an output indicative of the electric field(s) induced in the conductive element(s) by the incident electromagnetic wavefield (task 310). As described in greater detail below, in an exemplary embodiment, an incident wavefield energy metric is multiplied by the surface electromagnetic impedance to obtain a value indicative of the induced current(s) in the conductive element(s). For example, in accordance with one embodiment, the resistive part of the electromagnetic impedance matrix is multiplied by the time averaged energy density (U) of the incident wavefield and divided by the modal density (v) of electromagnetic modes in the dielectric medium surrounding the conductive element(s) to obtain a mean squared current induced in the conductive element(s) based on the mean (or ensemble average) of the square of the induced magnetic field on the surface of the conductive element(s), as described in greater detail below with reference to equations (1)-(18) and (92)-(93). In an exemplary embodiment, in addition to determining a metric indicative of the induced current in the conductive element(s) using the diffuse field reciprocity principle, the process 300 also determines a voltage recovery matrix for the conductive element(s) as described in greater detail below in the context of FIG. 5 and determines a metric indicative of the induced voltage in the conductive element(s) using the voltage recovery matrix and the induced magnetic field. As described above in the context of FIG. 2 and in greater detail below in the context of FIGS. 8, 10, 12-15 and 17, the processing system 204 may display, present or otherwise provide one or more graphical representations of the current and/or voltage induced in the conductive element(s) on the display device 206 for review and analysis by the user.

Figure 4:
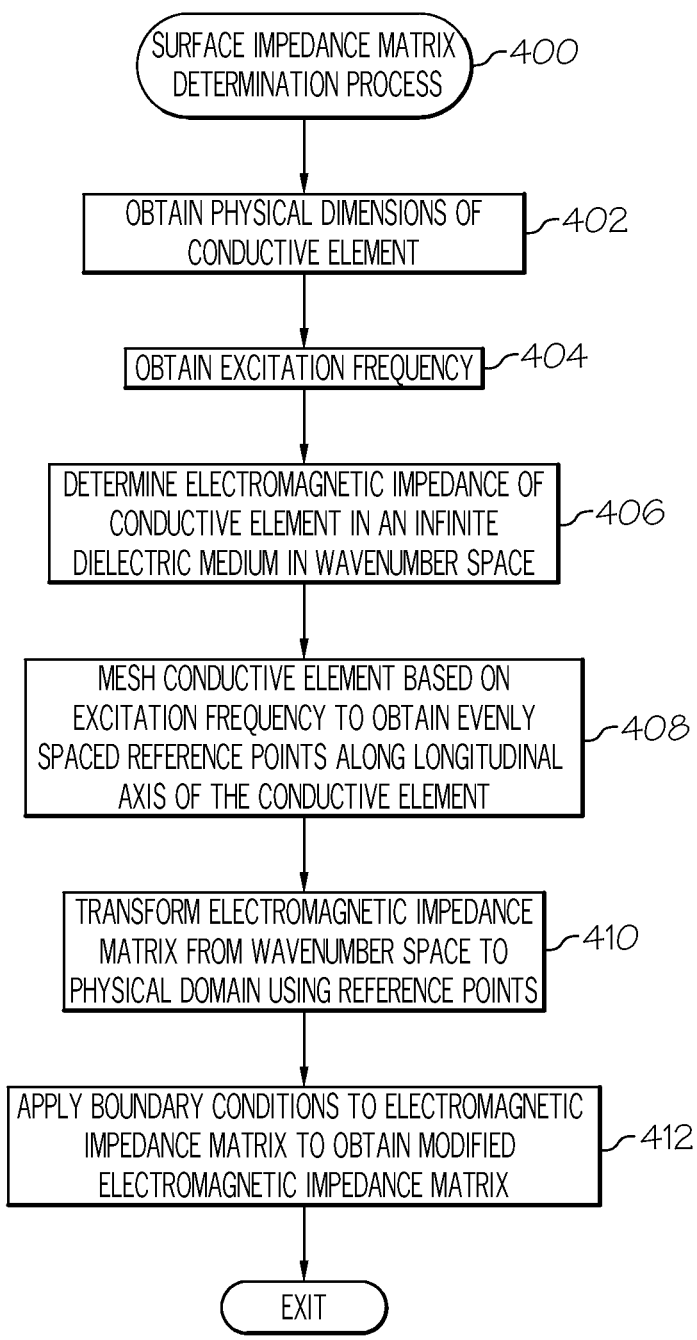
FIG. 4 is a flow diagram that illustrates an exemplary surface impedance matrix determination process suitable for use with the computing system of FIG. 2 in conjunction with the induced field determination process of FIG. 3.

FIG. 4 is a flow chart that depicts an exemplary embodiment of a surface impedance matrix determination process 400 that may be performed (e.g., by processing system 204 as part of process 300) to determine an impedance matrix that is associated with electromagnetic radiation from the surface of a conductive element into an infinite dielectric medium. The various tasks performed in connection with the illustrated process 400 may be performed by software, hardware, firmware, or any combination thereof. For illustrative purposes, the following description of illustrated processes may refer to elements mentioned above in connection with FIG. 1 and FIG. 2. It should be appreciated that the process 400 may include any number of additional or alternative tasks, the tasks need not be performed in the illustrated order and/or the tasks may be performed concurrently, and/or the process 400 may be incorporated into a more comprehensive procedure or process having additional functionality not described in detail herein. Moreover, one or more of the tasks shown and described in the context of FIG. 4 could be omitted from an embodiment of the respective process as long as the intended overall functionality remains intact.

In an exemplary embodiment, the process 400 begins by obtaining the excitation frequency for the incident electromagnetic wavefield and the physical dimensions of the conductive element (tasks 402, 404). As described above in the context of FIG. 3, in an exemplary embodiment, the excitation frequency for the incident electromagnetic wavefield and the physical dimensions of the conductive element are obtained from a user (e.g., via user input device 202). Using the excitation frequency and the physical dimensions of the conductive element, the process 400 continues by determining the surface electromagnetic impedance matrix for the conductive element in wavenumber space (or alternatively, the frequency domain) (task 406), as described in greater detail below with reference to equations (24)-(40). The process 400 continues by meshing the conductive element using the excitation frequency to determine a number of evenly spaced reference points along the longitudinal axis of the conductive element (task 408), as described in greater detail below with reference to equations (73)-(74), and then transforming the surface electromagnetic impedance matrix from wavenumber space to the physical domain (task 410) by performing a Fourier transform using the reference points, as described in greater detail below with reference to equations (75)-(78). In an exemplary embodiment, the process 400 continues by applying boundary conditions to the transformed surface electromagnetic impedance matrix to obtain a modified surface electromagnetic impedance matrix in the physical domain (task 412), as described in greater detail below with reference to equation (86). In an exemplary embodiment, the modified surface electromagnetic impedance matrix is utilized in the process 300 of FIG. 3 by applying the diffuse field reciprocity principle to the modified surface electromagnetic impedance matrix to determine metrics indicative of current induced in the conductive element, as described above and in greater detail below with reference to equations (92)-(93).

Figure 5:
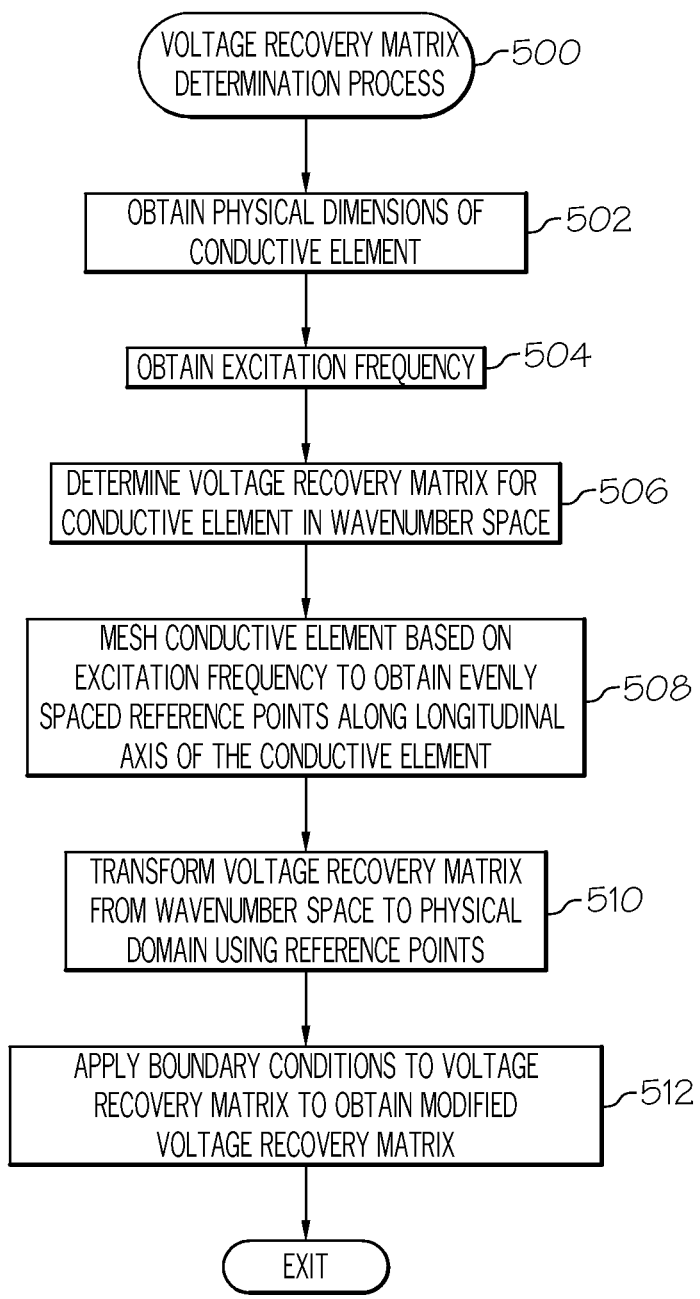
FIG. 5 is a flow diagram that illustrates an exemplary voltage recovery matrix determination process suitable for use with the computing system of FIG. 2 in conjunction with the induced field determination process of FIG. 3.

FIG. 5 is a flow chart that depicts an exemplary embodiment of a voltage recovery matrix determination process 500 that may be performed (e.g., by processing system 204 as part of process 300) to determine a voltage recovery matrix for determining the induced voltage in a conductive element. The various tasks performed in connection with the illustrated process 500 may be performed by software, hardware, firmware, or any combination thereof. For illustrative purposes, the following description of illustrated processes may refer to elements mentioned above in connection with FIG. 1 and FIG. 2. It should be appreciated that the process 500 may include any number of additional or alternative tasks, the tasks need not be performed in the illustrated order and/or the tasks may be performed concurrently, and/or the process 500 may be incorporated into a more comprehensive procedure or process having additional functionality not described in detail herein. Moreover, one or more of the tasks shown and described in the context of FIG. 5 could be omitted from an embodiment of the respective process as long as the intended overall functionality remains intact.

In an exemplary embodiment, the process 500 begins by obtaining the excitation frequency for the incident electromagnetic wavefield and the physical dimensions of the conductive element (tasks 502, 504). As described above in the context of FIG. 3, in an exemplary embodiment, the excitation frequency for the incident electromagnetic wavefield and the physical dimensions of the conductive element are obtained from a user (e.g., via user input device 202). Using the excitation frequency and the physical dimensions of the conductive element, the process 500 continues by determining the voltage recovery matrix for the conductive element in wavenumber space (or alternatively, the frequency domain) (task 506), as described in greater detail below with reference to equations (79)-(82). The process 500 continues by meshing the conductive element using the excitation frequency to determine a number of evenly spaced reference points along the longitudinal axis of the conductive element (task 508) in a similar manner as described herein in the context of the surface impedance matrix, and then transforms the voltage recovery matrix from wavenumber space to the physical domain (task 510), as described in greater detail below with reference to equations (83)-(85). In an exemplary embodiment, the process 500 continues by applying boundary conditions to the transformed voltage recovery matrix to obtain a modified voltage recovery matrix in the physical domain (task 512), as described in greater detail below with reference to equation (87). In an exemplary embodiment, the modified voltage recovery matrix is utilized in the process 300 of FIG. 3 to determine metrics indicative of voltage induced in the conductive element based on the induced magnetic field obtained by applying the diffuse field reciprocity principle, as described above and in greater detail below.

Having thus generally described the exemplary systems and processes for applying diffuse field reciprocity to determine the magnitude of currents and/or voltages induced in a conductive element by an incident electromagnetic wavefield, the diffuse field reciprocity principle and exemplary applications thereof will now be described in greater detail with reference to FIGS. 6-17.

Diffuse Field Reciprocity Principle

Figure 6:
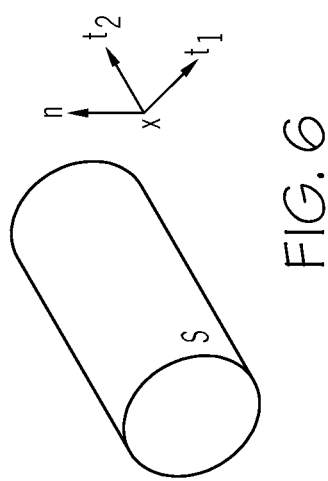
FIG. 6 is a perspective view of an exemplary conductive element for purposes of illustrating the diffuse field reciprocity principle described in the context of the induced field determination process of FIG. 3 applied to a single wire transmission line system.

FIG. 6 depicts a surface S representative of a conductive element (or a portion thereof), which consist of a number of cylindrical surfaces representing the combined surface of a multiple wire system. At a general point x on the surface the unit normal vector pointing into the dielectric is denoted by n(x) and two orthogonal unit tangent vectors are denoted by $t_1(x)$ and $t_2(x)$. The electric and magnetic field vectors at x, E(x) and H(x) respectively, can be expressed in terms of normal and tangential components in the form $$E(x)=E_1(x)t_1(x)+E_2(x)t_2(x)+E_n(x)n(x), \quad (1)$$

$$H(x)=H_1(x)t_1(x)+H_2(x)t_2(x)+H_n(x)n(x). \quad (2)$$

The field components are taken to be harmonic in time with frequency ω, and the variables in equations (1) and (2) are taken to represent complex amplitudes so that, for example, the time history of the first tangential electric component $E_1$ is given by $Re\{E_1 e^{-i\omega t}\}$. With this notation, the time average of the total electromagnetic power radiated by the surface can be written as $$P = (1/2)Re\left\{\int_S (E \times H^*) \cdot n ds\right\} \quad (3)$$

$$= (1/2)Re\left\{\int_S (E_1 H_2^* - E_2 H_1^*) ds\right\}.$$

To aid a numerical analysis of the system, the tangential components of the magnetic field can be expressed in terms of a finite number of generalized coordinates so that $$H_j(x) = \sum_{n=1}^{N} h_{jn}\phi_n(x), \; j = 1, 2, \tag{4}$$

where $\phi_n(x)$ (n=1, 2, . . . , ∞) is a complete set of basis functions defined over the surface S, and $h_{jn}$(n=1, 2, . . . , N) is a finite set of generalized coordinates used to approximate the magnetic field component $H_j(x)$. Similarly, a set of generalized coordinates $e_{jn}$ can be introduced to describe the electric field, with the definition $$e_{jn} = \int_S E_j(x)\phi_n(x)ds, \; j = 1, 2. \tag{5}$$

The tangential field components can then represented by the vectors $$e = \begin{pmatrix} -e_2 \\ e_1 \end{pmatrix}, h = \begin{pmatrix} h_1 \\ h_2 \end{pmatrix}, \tag{6, 7}$$

where $e_1$, for example, contains the generalized coordinates $e_{1n}$. The ordering of the components in equations (6) and (7) has been chosen so that, by virtue of equations (3)-(5), the following relation holds:

$$P=(\tfrac{1}{2})Re(h^{*T}e). \tag{8}$$

It can be noted that a requirement for equation (8) to apply actually underlies the definition of the generalized coordinates given by equations (4) and (5). If the functions $\phi_n(x)$ are orthonormal, then equations (4) and (5) are mathematically alike, and there is no distinction between the definition of the generalized coordinates for the electric and magnetic fields. However, in many approximate methods (for example the finite element method) the functions $\phi_n(x)$ are not orthonormal, and in this case the magnetic field generalized coordinates are not given by the magnetic equivalent of equation (5); rather, equation (4) can be inverted by using the method of weighted residuals to yield the generalized coordinates in terms of the magnetic field.

The electromagnetic field in an infinite dielectric medium must satisfy Maxwell's equations. Taking the case in which there are no internal sources of electromagnetic radiation within the dielectric medium, and assuming that the Sommerfeld radiation conditions apply at infinity, these equations can be solved (analytically or numerically) to yield a relation between the tangential electric and magnetic field components on S. This relation can be expressed in terms of an impedance matrix $Z_D$ such that $$Z_D h=e. \tag{9}$$

Now the impedance matrix can be expressed as the sum of a Hermitian component $Z_{DH}$ and an anti-Hermitian component $Z_{DA}$ so that $$Z_D=(Z_D+Z^*_D{}^T)/2+(Z_D-Z^*_D{}^T)/2=Z_{DH}+Z_{DA}. \tag{10}$$

One physically significant feature of these two components is that the power radiated by the surface is determined completely by $Z_{DH}$, since it follows from equations (8)-(10) that $$P=(\tfrac{1}{2})h^{*T}Z_{DH}h. \tag{11}$$

In acoustical or mechanical terminology, $Z_{DH}$ is referred to as the resistive part of the impedance matrix, associated with waves which propagate to infinity, while $Z_{DA}$ is referred to as the reactive part, associated with near-field effects. Two extensions to equation (9) are now considered: (i) the addition of incident electromagnetic waves in the dielectric, and (ii) the inclusion of the impedance matrix, $Z_C$ say, associated with the material that lies within the surface S. This leads to the pair of equations $$Z_D(h-h_{inc})=e-e_{inc}, \; Z_C h=-e, \tag{12, 13}$$

where e and h are the total field components on S, and $e_{inc}$ and $h_{inc}$ are the field components arising from the incident electromagnetic waves (in the absence of any reflection or diffraction at S). The sign convention associated with equation (13) is chosen to ensure that the power given by the analogy of equation (11) is in the direction of the inwards pointing normal vector, i.e. into the material associated with the impedance matrix. Now equations (12) and (13) yield $$(Z_D+Z_C)h=Z_D h_{inc}-e_{inc}=-e_b, \tag{14}$$

where $e_b$ is referred to herein as the blocked electric field, i.e., the surface tangential electric field that would result were the inner material such that h=0. The terminology "blocked" is often used in acoustics; for example the blocked acoustic pressure in a sound field containing an object is defined as the pressure obtained when the acoustic velocity normal to the surface of the object is enforced to be zero. In the present context the electric and magnetic fields are loosely analogous to the acoustic pressure and the normal velocity.

When the incident electromagnetic waves on the surface S constitute a random diffuse field, the diffuse field reciprocity principle applies so that $$E[e_b \; e_b^{*T}] = \left(\frac{4U}{\pi v}\right) Z_{DH}, \tag{15}$$

where E[ ] represents the ensemble average, taken over realizations of the random diffuse field. In this result, $Z_{DH}$ is the impedance matrix associated with an infinite dielectric (i.e. with Sommerfeld radiation boundary conditions), while the diffuse waves are taken to be contained in a physical dielectric of finite extent; U is the time averaged energy of the diffuse field, and v is the modal density of electromagnetic modes in the dielectric (i.e. the average number of natural frequencies within a unit frequency band). These quantities are given by $$U=(\tfrac{1}{2})\mu V E[|H|^2], \; v=V\omega^2/(\lambda^2 c^3), \tag{16, 17}$$

where $\mu$ and V are respectively the permeability and volume of the dielectric, c is the speed of light, and $\omega$ is the frequency (in radians) of the incident wavefield. It can be noted that a diffuse field is by definition statistically homogenous, and so $E[|H|^2]$ is independent of spatial position. Equation (15) in conjunction with equation (14) yields a very efficient solution for the cross-spectrum of the surface magnetic field induced by the incident diffuse wavefield:

$$E[hh^{*T}] = \left(\frac{4U}{\pi v}\right)(Z_D + Z_C)^{-1} Z_{DH}(Z_D + Z_C)^{-T^*}. \tag{18}$$

The application of the diffuse field reciprocity principle will now be described in greater detail in the context of the surface S representing the surface of one or more transmission lines. For purposes of explanation, in each case described below, it is assumed that the transmission line is composed of a number of wires of circular cross-section which each run parallel to the $x_3$-axis. The surface electromagnetic field on each wire is taken to be constant around the circumference of the wire so that, in terms of cylindrical waveguide theory, only the n=0 components are considered to be significant over the frequency range of interest. For wires in close proximity, the present theory can be extended to include higher order waveguide modes, at the cost of additional algebraic complexity. However, for purposes of explaining the application of the diffuse field reciprocity principle, the n=0 restriction is adopted with the consequent assumption that the wires are not too closely spaced. The surface electric and magnetic fields are thus represented by field variables, $e_j(x_3)$ and $h_j(x_3)$ respectively, which depend only upon the coordinate $x_3$, and these variables are taken to be ordered such that equation (8) applies, as described in greater detail below. The field variables are represented by generalized coordinates $h_{jn}$ and $e_{jn}$, which are defined analogously to equations (4) and (5) in the form $$h_j(x_3) = \sum_{n=1}^{N} h_{jn}\phi_n(x_3), \quad e_{jn} = \int_L e_j(x_3)\phi_n(x_3)dx_3, \quad (19, 20)$$

where L is the domain of the transmission line. In the detailed analysis of transmission lines it is analytically convenient to consider the Fourier transform of the field variables, so that, for example, the Fourier transform $\hat{h}_j(k_3)$ is considered rather than $h_j(x_3)$, where $$\hat{h}_j(k_3) = \frac{1}{\sqrt{2\pi}} \int_L h_j(x_3)e^{-ik_3x_3}dx_3, \quad (21)$$

$$h_j(k_3) = \frac{1}{\sqrt{2\pi}} \int_{-\infty}^{\infty} \hat{h}_j(k_3)e^{ik_3x_3}dx_3, \quad (22)$$

and $k_3$ is the wavenumber in the $x_3$-direction. With this notation, a dielectric impedance matrix in wavenumber space, $\hat{Z}_D(k_3)$ say, can be defined such that $$\hat{e}_j(k_3) = \sum_r \hat{Z}_{Djr}(k_3)\hat{h}_r(k_3). \quad (23)$$

Likewise, a blocked electric field $\hat{e}_{bj}(k_3)$ can be defined as the Fourier transform of the blocked electric field in physical space, $e_{bj}(x_3)$.

Diffuse Field Reciprocity in Wavenumber Space

The impedance matrix $Z_D$ in generalized coordinates can be deduced by applying Parseval's theorem to equation (20) and then employing equation (23) to yield $$e_{jn} = \int_{-\infty}^{\infty} \hat{e}_j(k_3)\hat{\phi}_n^*(k_3)dk_3 \quad (24)$$
$$= \sum_r \int_{-\infty}^{\infty} \hat{Z}_{Djr}(k_3)\hat{h}_r(k_3)\hat{\phi}_n^*(k_3)dk_3$$
$$= \sum_{rm} Z_{Djnrm}h_{rm}.$$

where the final equality in this result arises from the definition of $Z_D$. Hence $$Z_{Djnrm} = \int_{-\infty}^{\infty} \hat{Z}_{Djr}(k_3)\hat{\phi}_m(k_3)\hat{\phi}_n^*(k_3)dk_3. \quad (25)$$

The blocked electric field can be expressed in generalized coordinates as $$e_{bjn} = \int_L e_{bj}(x_3)\phi_n(x_3)dx_3 = \int_{-\infty}^{\infty} \hat{e}_{bj}(k_3)\hat{\phi}_n^*(k_3)dk_3, \quad (26)$$

and it follows that $$E[e_{bjn}e_{brm}^*] = \int_{-\infty}^{\infty}\int_{-\infty}^{\infty} E[\hat{e}_{bj}(k_3)\hat{e}_{br}^*(k_3')]\hat{\phi}_m(k_3')\hat{\phi}_n^*(k_3)dk_3dk_3'. \quad (27)$$

Now, for the diffuse field reciprocity equation (15) to apply in generalized coordinates, it follows from equations (25) and (27) that the following condition must be met in wavenumber space $$E[\hat{e}_{bj}(k_3)\hat{e}_{br}^*(k_3')]=(4U/\pi v)\delta(k_3-k_3')\hat{Z}_{DHjr}(k_3), \quad (28)$$

where $\hat{Z}_{DH}(k_3)$ is the Hermitian part of $\hat{Z}_D(k_3)$. This equation can be simplified slightly by considering the nature of the incident diffuse field which gives rise to the blocked electric field. The magnetic field associated with the diffuse field can be written in terms of its Fourier transform in the form $$H(x) = \frac{1}{\sqrt{2\pi}} \int_{-k}^{k} \hat{H}(x_1, x_2, k_3)e^{ik_3x_3}dk, \quad (29)$$

where $k=\omega/c$ is the wavenumber of each wave component of the diffuse field, and it has been noted that the projected wavenumber $k_3$ cannot exceed k. It follows that $$E[|H|^2] = \quad (30)$$
$$\frac{1}{2\pi}\int_{-k}^{k}\int_{-k}^{k} E[\hat{H}(x_1, x_2, k_3) \cdot \hat{H}^*(x_1, x_2, k_3')]e^{i(k_3-k_3')x_3}dk_3dk_3'.$$

The left hand side of equation (30) is independent of x, since the diffuse field is statistically homogeneous, and furthermore for a three-dimensional diffuse field the energy in the field is evenly distributed among the wavenumbers $k_3$. Applying these considerations to equation (30) leads to the conclusion that $$E[\hat{H}(x_1,x_2,k_3)\cdot\hat{H}^*(x_1,x_2,k_3')]=(\pi/k)E[|H|^2]\delta(k_3-k_3'). \quad (31)$$

Now, the diffuse field can be represented as a collection of plane waves of various headings and polarizations, and the waves which contribute to $\hat{H}(x_1, x_2, k_3)$ will all have the same heading $\beta$ relative to the $x_3$-axis, which is given by $\beta=\cos^{-1}(k_3/k)$. These waves will however have a range of azimuth angles $\phi$ and polarization angles $\psi$. If $\hat{f}_{bj}(\phi, \psi, k_3)$ is defined as the blocked electric field associated with an incident wave of unit amplitude (i.e. the magnetic vector of the wave is of unit amplitude), and specified heading, azimuth angle, and polarization, then $$E[\hat{e}_{bj}(k_3)\hat{e}_{br}^*(k_3')]=\langle \hat{f}_{bj}(\phi,\psi,k_3)\hat{f}_{br}^*(\phi,\psi,k_3')\rangle_{\phi,\psi} \times E[\hat{H}(x_1,x_2,k_3)\cdot\hat{H}^*(x_1,x_2,k_3')], \quad (32)$$

where the first term on the right hand side represents an average over the azimuth and polarization angles. Equations

(31) and (32), together with equations (16) and (17), imply that equation (28) can be rewritten in the form $$\langle \hat{f}_{bj}(\phi,\psi,k_3)\hat{f}^*_{br}(\phi,\psi,k'_3)\rangle_{\phi,\psi} = (2\mu\omega/k^2)\hat{Z}_{DHjr}(k_3). \quad (33)$$

If equation (33) is satisfied, then the diffuse field reciprocity equation (15) holds in generalized coordinates. The validity of equation (33) is explored below for a range of transmission lines and/or wiring configurations.

Single Wire Transmission Line

In the case of a single wire running through a dielectric material, the surface S consists of the cylindrical outer surface of the wire. For a prescribed axial wavenumber $k_3$ the full solution to Maxell's equations in the dielectric medium, with Sommerfeld radiation boundary conditions, consists of transverse magnetic (TM) and transverse electric (TE) cylindrical waves, of order $n=0, \pm 1, \ldots, \pm\infty$, such that the functional dependency of the electromagnetic field on the cylindrical polar angle $\theta$ has the form $\exp(in\theta)$. Only the zero order terms ($n=0$) are of interest here, and in this case the TM and TE waves are uncoupled on the cylindrical surface S: the non-zero surface field components for the TM waves are (in cylindrical polar coordinates, with $z=x_3$) $E_z$ and $H_\theta$, while those associated with the TE waves are $E_\theta$ and $H_z$. The following analysis is restricted to the case of TM waves, since these waves are responsible for any axial current along the wire. For $n=0$, the TM surface field components are $$E_z = AH_0^{(1)}(\lambda a)e^{ik_3x_3}, \quad (34)$$

$$H_\theta = A(ik^2/\mu\omega\lambda)H_0^{(1)'}(\lambda a)e^{ik_3x_3}, \quad (35)$$

where $a$ is the radius of the wire, A is the cylindrical wave amplitude, and $$\lambda = (k^2 - k_3^2)^{1/2}. \quad (36)$$

The field variables in wavenumber space, $\hat{e}_j(k_3)$ and $\hat{h}_j(k_3)$ (discussed above), can now be defined on the basis of equations (34) and (35) as $$\hat{e}_1(k_3) = -AH_0^{(1)}(\lambda a), \quad (37)$$

$$\hat{h}_1(k_3) = 2\pi a A(ik^2/\mu\omega\lambda)H_0^{(1)'}(\lambda a). \quad (38)$$

The negative sign is included in equation (37), together with the factor of $2\pi a$ in equation (38), to ensure that the power radiated by the wire is given by equation (8). The variable given by equation (38) can be identified as the integral of the circumferential component of the magnetic field around the circumference of the wire, and from the Maxwell-Ampere law this is actually the current in the wire. It follows from equations (23), (37) and (38) that the impedance matrix of the dielectric (in this case a scalar) in wavenumber space is given by $$\hat{Z}_D(k_3) = \left(\frac{i\mu\omega\lambda}{2\pi ak^2}\right)\left[\frac{H_0^{(1)}(\lambda a)}{H_0^{(1)'}(\lambda a)}\right]. \quad (39)$$

The Hermitian part of the impedance is then $$\hat{Z}_{DH}(k_3) = \begin{cases} \mu\omega(\pi ak)^{-2}|H_0^{(1)'}(\lambda a)|^{-2} & k_3 \le k \\ 0 & k_3 > k \end{cases}, \quad (40)$$

where the Bessel function Wronskian properties have been used to simplify the result.

For purposes of demonstrating the validity of equation (33), an expression must be derived for the blocked electric field $\hat{f}_{b,1}$ arising from an incident plane electromagnetic wave. To this end, the field associated with an incident plane wave of magnetic amplitude $H_{amp}$ and axial wavenumber $k_3$ can be written in the form $$H = H_{amp}[\cos\psi n_1 + \sin\psi n_2]e^{ik\cdot x}, \quad (41)$$

$$E = H_{amp}\eta[\sin\psi n_1 - \cos\psi n_2]e^{ik\cdot x}, \quad (42)$$

where $\eta = \sqrt{\mu/\epsilon}$ and $$n_1 = (-\sin\phi\cos\phi 0), \quad (43)$$

$$n_2 = (-\cos\beta\cos\phi - \cos\beta\sin\phi\sin\beta), \quad (44)$$

$$k = (k\cos\phi\sin\beta k\sin\phi\sin\beta k_3). \quad (45)$$

Here $\beta$ is the angle of incidence to the $x_3$-axis, $\phi$ is the azimuth angle of incidence, measured in the $x_1$-$x_2$ plane, and $\psi$ is the polarization of the wave, measured in a plane perpendicular to the propagation direction. From these definitions, equation (36) can be rewritten as $\lambda = k\sin\beta$. Now on the surface S, the Cartesian position vector x and two unit tangent vectors $t_z$ and $t_\theta$ can be written in terms of the cylindrical polar angle $\theta$ in the form $$x = (a\cos\theta a\sin\theta x_3), t_z = (0\ 0\ 1), \quad (46,47)$$

$$t_\theta = (-\sin\theta\cos\theta 0). \quad (48)$$

With this notation, the $n=0$ axial surface component of the incident electric field is given by $$\hat{e}_{inc,1}(k_3) = -(2\pi)^{-1}e^{ik_3x_3}\int_0^{2\pi} E\cdot t_z d\theta = H_{amp}J_0(\lambda a)\eta\cos\psi\sin\beta, \quad (49)$$

and similarly, the $n=0$ circumferential surface component of the incident magnetic field is given by $$\hat{h}_{inc,1}(k_3) = 2\pi a(2\pi)^{-1}e^{-ik_3x_3}\int_0^{2\pi} H\cdot t_\theta d\theta \quad (50)$$
$$= -iH_{amp}J_0'(\lambda a)2\pi a\cos\psi.$$

By using equations (14), (39), (49) and (50), the blocked incident electric field can be evaluated as $$\hat{e}_{b,1}(k_3) = \hat{e}_{inc,1}(k_3) - \hat{Z}_D(k_3)\hat{h}_{inc,1}(k_3) \quad (51)$$
$$= \left[\frac{H_{amp}\mu\omega\lambda\cos\psi}{k^2 H_0^{(1)'}(\lambda a)}\right] \times$$
$$\{J_0(\lambda a)H_0^{(1)'}(\lambda a) - J_0'(\lambda a)H_0^{(1)}(\lambda a)\}.$$

By definition, $\hat{f}_{b,1}$ is given by the value of $\hat{e}_{b,1}$ under the condition $H_{amp} = 1$. It can therefore be shown that (for $k_3 \le k$)

$$\langle|\hat{f}_{b,1}|^2\rangle_{\phi,\psi} = 2(\mu\omega)^2(\pi ak^2)^{-2}|H_0^{(1)'}(\lambda a)|^{-2} = (2\mu\omega/k^2)\hat{Z}_{DH}(k_3), \quad (52)$$

where the Bessel function Wronskian properties have been employed. For $k_3 > k$ the corresponding result is zero, in line with equation (40). It follows from equation (52) that equation (33) is satisfied, thus proving the validity of the diffuse field reciprocity principle for a single wire.

Two Wire Transmission Line System

Figure 7:
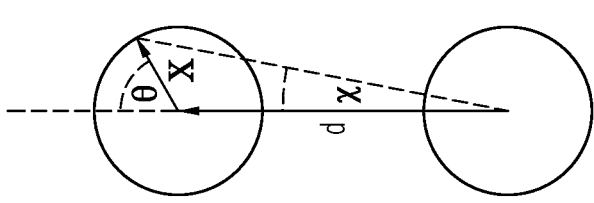
FIG. 7 is a schematic view of an exemplary arrangement of a pair of conductive elements for purposes of illustrating the diffuse field reciprocity principle described in the context of the induced field determination process of FIG. 3 applied to a two wire transmission line system.

The previous analysis is extended in this section to the case of two parallel wires, each of radius $a$, which are spaced a distance $d$ apart: the center of one wire runs along the line (0, 0, $x_3$), while the other runs along (–d, 0, $x_3$). FIG. 7 depicts a simplified representation of a two wire transmission line system for purposes of explanation. For a given axial wavenumber $k_3$, the solution to Maxwell's equations in the dielectric medium can be represented as the sum of two sets of cylindrical waves, each set being centered on one of the wires. Thus for n=0 TM waves, the electromagnetic field can be represented as a cylindrical wave of amplitude $A_1$ centered on the first wire, together with a cylindrical wave of amplitude $A_2$ centered on the second wire. In this case, equation (37) for the axial electric field variable on the surface of the first wire is modified to become $$\hat{e}_1(k_3) = -A_1 H_0^{(1)}(\lambda a) - A_2 (2\pi)^{-1} \int_0^{2\pi} H_0^{(1)}(\lambda |x+d|) d\theta, \quad (53)$$

where the second term represents the contribution from the wave centered on the second wire, and the vector d joins the centers of the two wires as shown in FIG. 7. The integral which appears in equation (53) can be evaluated to yield $$\hat{e}_1(k_3) = -A_1 H_0^{(1)}(\lambda a) - A_2 H_0^{(1)}(\lambda d) J_0(\lambda a). \quad (54)$$

Similarly, the circumferential magnetic field variable on the surface of the first wire is modified from equation (38) to become $$\hat{h}_1(k_3) = 2\pi a (ik^2 / \mu\omega\lambda) \{A_1 H_0^{(1)\prime}(\lambda a) + \quad (55)$$
$$A_2 (2\pi)^{-1} \int_0^{2\pi} H_0^{(1)\prime}(\lambda |x+d|) \cos(\theta - \chi) d\theta\}$$
$$= 2\pi a (ik^2/\mu\omega\lambda) \{A_1 H_0^{(1)\prime}(\lambda a) - A_2 H_0^{(1)}(\lambda d) J_1(\lambda a)\},$$

where the angles $\theta$ and $\chi$ are shown in FIG. 7. Equations similar to equations (54) and (55) can be derived for the second wire, to yield $$\begin{pmatrix} \hat{e}_1 \\ \hat{e}_2 \end{pmatrix} = -\begin{pmatrix} H_0^{(1)}(\lambda a) & H_0^{(1)}(\lambda d) J_0(\lambda a) \\ H_0^{(1)}(\lambda d) J_0(\lambda a) & H_0^{(1)}(\lambda a) \end{pmatrix} \begin{pmatrix} A_1 \\ A_2 \end{pmatrix} = P_1 A, \quad (56)$$

$$\begin{pmatrix} \hat{h}_1 \\ \hat{h}_2 \end{pmatrix} = \quad (57)$$
$$\left(\frac{2\pi a i k^2}{\mu\omega\lambda}\right) \times \begin{pmatrix} H_0^{(1)\prime}(\lambda a) & -H_0^{(1)}(\lambda d) J_1(\lambda a) \\ -H_0^{(1)}(\lambda d) J_1(\lambda a) & H_0^{(1)\prime}(\lambda a) \end{pmatrix} \begin{pmatrix} A_1 \\ A_2 \end{pmatrix} = P_2 A,$$

where the matrices $P_1$ and $P_2$ are defined accordingly. The impedance matrix of the dielectric medium in wavenumber space then follows as $$\hat{Z}_D(k_3)\hat{h} = \hat{e}, \quad \hat{Z}_D(k_3) = P_1 P_2^{-1}. \quad (58, 59)$$

The electric and magnetic fields arising from an incident plane wave can be derived by extending equations (49) and (50) to yield $$\hat{e}_{inc} = H_{amp} J_0(\lambda a) \eta \cos\psi \sin\beta \begin{pmatrix} 1 \\ e^{-ikd\cos\varphi\sin\beta} \end{pmatrix}, \quad (60)$$

$$\hat{h}_{inc} = -i H_{amp} J_0'(\lambda a) 2\pi a \cos\psi \begin{pmatrix} 1 \\ e^{-ikd\cos\varphi\sin\beta} \end{pmatrix}, \quad (61)$$

and the blocked electric field is then given by $$\hat{e}_b = \hat{e}_{inc} - \hat{Z}_D \hat{h}_{inc}. \quad (62)$$

Equations (59) and (62) can be used to explore the validity of equation (33) for the two wire system. An important special case is that of the transmission mode of the system, in which the current in the second wire is equal in magnitude and opposite in sign to that in the first wire, which implies that $A_2 = -A_1$. Field variables $\hat{h}_T(k_3)$ and $\hat{e}_T(k_3)$ can be defined for the transmission mode such that $$\hat{h} = \hat{h}_T \begin{pmatrix} 1 \\ -1 \end{pmatrix}, \quad (63, 64)$$
$$\hat{e}_T = (1 \quad -1)\hat{e},$$

and it can then be shown from equations (56)-(59) that the associated impedance is given by $$\hat{Z}_{DT}(k_3) = \frac{\hat{e}_T}{\hat{h}_T} = \left(\frac{i\mu\omega\lambda}{\pi a k^2}\right) \left[\frac{H_0^{(1)}(\lambda a) - H_0^{(1)}(\lambda d) J_0(\lambda a)}{H_0^{(1)\prime}(\lambda a) + H_0^{(1)}(\lambda d) J_1(\lambda a)}\right]. \quad (65)$$

After some algebra, it follows that the Hermitian part of the impedance is $$\hat{Z}_{DH}(k_3) = \begin{cases} \left(\frac{2\mu\omega}{\pi^2 a^2 k^2}\right)[1 - J_0(\lambda d)] \times \\ \left|H_0^{(1)\prime}(\lambda a) + H_0^{(1)}(\lambda d) J_1(\lambda a)\right|^{-2} & k_3 \leq k \\ 0 & k_3 > k \end{cases}. \quad (66)$$

Now the blocked electric field associated with the transmission mode can be written in the form $$\hat{e}_{bT} = (1 \quad -1)\hat{e}_b \quad (67)$$
$$= \left(\frac{-2\mu\omega H_{amp} \cos\psi}{\pi a k^2}\right) \times$$
$$\left[\frac{1 - e^{-ikd\cos\varphi\sin\beta}}{H_0^{(1)\prime}(\lambda a) + H_0^{(1)}(\lambda d) J_1(\lambda a)}\right],$$

and by definition the variable $\hat{f}_{bT}$ is given by this result under the condition $H_{amp} = 1$. It thus follows that (for $k_3 \leq k$)

$$\langle |\hat{f}_{bT}|^2 \rangle_{\varphi,\psi} = \left(\frac{2\mu\omega}{\pi a k^2}\right)^2 [1 - J_0(\lambda d)] \times \quad (68)$$
$$\left|H_0^{(1)\prime}(\lambda a) + H_0^{(1)}(\lambda d) J_1(\lambda a)\right|^{-2}$$
$$= (2\mu\omega/k^2) \hat{Z}_{DH}(k_3),$$

and the diffuse field reciprocity principle is valid for the transmission mode in a two wire system.

Surface Electromagnetic Impedance Matrix Determination for a Conducting Wire

The preceding discussion considered the properties of the impedance matrix $Z_D$ associated with an infinite dielectric medium surrounding a transmission line. In this section the matrix $Z_C$ which appears in equation (13) is considered: this is the impedance matrix associated with the conducting material in the transmission line. The aim is not to demonstrate that the diffuse field reciprocity principle applies to this impedance, since clearly the conducting material will not carry a diffuse field, but rather to derive expressions for the electromagnetic impedance at the surface of the conducting material diffuse field reciprocity principle can be applied. For a single conducting wire of radius a, the impedance (a scalar in this case) follows from a very similar argument to that used to derive the dielectric impedance, equation (39). The Hankel function $H_0^{(1)}$ used to describe the outer solution to Maxwell's equations must be replaced by the Bessel function $J_0$, and a sign change must be introduced to account for the direction of the inwards pointing normal; this procedure yields $$\hat{Z}_C(k_3) = \left(\frac{-i\mu_c \omega \lambda_c}{2\pi a k_c^2}\right)\left[\frac{J_0(\lambda_c a)}{J_0'(\lambda_c a)}\right], \tag{69}$$

where $$k_c^2 = \omega^2 \mu_c (\varepsilon_c + i\sigma_c / \omega), \tag{70, 71}$$
$$\lambda_c^2 = k_c^2 - k_3^2,$$

and $k_c$, $\mu_c$, $\varepsilon_c$, and $\sigma_c$ are, respectively, the wavenumber, permeability, permittivity and conductance of the wire material. For many conducting materials $\sigma_c \gg \varepsilon_c \omega$ and equation (69) can be approximated as $$\hat{Z}_C(k_3) = \left(\frac{1-i}{2\pi a}\right)\left(\frac{\omega \mu_c}{2\sigma_c}\right)^{1/2}. \tag{72}$$

It can be noted that the impedance given by equation (72) is independent of $k_3$, hence under this approximation the material is locally reacting, i.e. the Fourier transform of $\hat{Z}_C$ is proportional to the delta function $\delta(x_3)$. For a single wire transmission line, equation (72) can be employed directly in the analysis described above; for the transmission mode of a two wire transmission line this result must be multiplied by a factor of two, so that equation (65) is augmented by the result $\hat{Z}_{CT} = 2\hat{Z}_C$.

Numerical Calculation of Impedance Matrices

In order to numerically apply the foregoing theory to transmission lines, it is necessary to select the shape functions $\phi_n(x_3)$ which appear in equations (19) and (20). The approach taken here is to consider a number of evenly spaced reference points along the transmission line ($x_{3,n}$ say, with $x_{3,n} - x_{3,n-1} = \Delta x$) and to employ a set of sinc functions centered on these points, so that $$\phi_n(x_3) = \text{sinc}[k_s(x_3 - x_{3,n})] = \frac{\sin[k_s(x_3 - x_{3,n})]}{k_s(x_3 - x_{3,n})}, \tag{73}$$

$$k_s = \pi / \Delta x. \tag{74}$$

As described above, the field variables for a single wire are represented by $e_1(x_3)$ and $h_1(x_3)$, while the field variables for the transmission mode response of a two wire system are represented by $e_T(x_3)$ and $h_T(x_3)$. For ease of explanation, the abbreviated notation $e(x_3)$ and $h(x_3)$ will be employed to represent either of these cases, and the corresponding generalized coordinates will be denoted by $e_n$ and $h_n$. It follows from equations (19), (20), and (73) that the generalized coordinates can be related to the values of the field variables at the reference points as follows $$h_n = h(x_{3,n}), \quad e_n = (\pi/k_s)e(x_{3,n}). \tag{75, 76}$$

Now, the Fourier transform of the shape functions is given by $$\hat{\phi}_n(k_3) = \begin{cases} (\pi/2)^{1/2} k_s^{-1} e^{-ik_s x_{3,n}} & |k_3| \le k_s \\ 0 & |k_3| > k_s \end{cases}, \tag{77}$$

so that the dielectric impedance matrix in generalized coordinates follows from equation (25) as $$Z_{Dnm} = \left(\frac{\pi}{2k_s^2}\right) \int_{-k_s}^{k_s} \hat{Z}_D(k_3) e^{-ik_3(x_{3,m} - x_{3,n})} dk_3 = Z_D(m-n). \tag{78}$$

The exponent in equation (78) contains the term $x_{3,n} - x_{3,n}$ which can also be written as $(m-n)\Delta x$; this means that $Z_{Dnm}$ is a function of $m-n$. The impedance matrix can therefore be evaluated very efficiently by using the Fast Fourier Transform (FFT) algorithm. With this approach the integral in equation (78) is evaluated for a range of exponents $\pm p\Delta x$, where p is an integer, and the results are then used to populate the matrix $Z_D$. This approach can similarly be used to calculate the impedance matrix $Z_C$ of the conducting material.

Voltage, Current, and Terminating Boundary Conditions

The electromagnetic field generated by a single wire, as given by equations (34) and (35), can be represented by a scalar potential $\Phi$ together with a vector potential A. Under the Lorentz gauge, the $x_3$-wise Fourier transform of the scalar potential is given by $$\hat{\Phi}(k_3) = -A(ik_3/\lambda^2)H_0^{(1)}(\lambda r). \tag{79}$$

By extension, the scalar potential associated with a two wire transmission line can be written as $$\hat{\Phi} = -(ik_3/\lambda^2)\{A_1 H_0^{(1)}(\lambda r_1) + A_2 H_0^{(1)}(\lambda r_2)\}, \tag{80}$$

where $A_1$ and $A_2$ are the amplitudes of the waves associated with the wires, and $r_1$ and $r_2$ are distances from the centers of the wires. The scalar potential represents a voltage measure, and for the transmission mode ($A_1 = -A_2$) the voltage across the wires is therefore given by $$\hat{V}_T(k_3) = (2\pi a)^{-1}\left\{\int_{C_1} \hat{\Phi} dl - \int_{C_2} \hat{\Phi} dl\right\} \tag{81}$$
$$= -2A_1(ik_3/\lambda^2)\{H_0^{(1)}(\lambda a) - H_0^{(1)}(\lambda d)J_0(\lambda a)\},$$

where $C_1$ and $C_2$ represent the circumferences of the wires in the $x_1$-$x_2$ plane, and d is the distance between the wire centers. It follows from equations (57), (63) and (81) that the transfer function between the voltage and the surface magnetic field is given by $$\hat{F}_T(k_3) = \frac{\hat{V}_T}{\hat{h}_T} = \left(\frac{-\mu\omega k_3}{\pi a k^2 \lambda}\right)\left[\frac{H_0^{(1)}(\lambda a) - H_0^{(1)}(\lambda d)J_0(\lambda a)}{H_0^{(1)\prime}(\lambda a) + H_0^{(1)}(\lambda d)J_1(\lambda a)}\right]. \quad (82)$$

The relationship between the voltage and the surface magnetic field in generalized coordinates then follows by analogy with equations (24) and (25), so that $$Fh_T = V_T, \quad (83, 84)$$

$$F_{nm} = \int_{-\infty}^{\infty} \hat{F}_T(k_3)\hat{\phi}_m(k_3)\hat{\phi}_n^*(k_3)\,dk_3,$$

$$V_{Tm} = (\pi/k_s)V_T(x_{3,m}). \quad (85)$$

The matrix F can be computed numerically by analogy with equations (77) and (78), and thus the voltage across the transmission line can be found from equation (83), once the surface magnetic field, $h_{Tn}=h_T(x_{3,n})$, is known. As described above with reference to equation (38), the surface magnetic field variable can be identified as the current in the wire. Although not detailed here, equations similar to equations (82)-(85) can also be derived for the case of a single wire.

As described above in the context of FIG. 4, the impedance matrix given by equation (78) should be modified for a transmission line or other conductive element having finite length L with prescribed boundary conditions at $x_3=0$ and $x_3=L$. If the line is modelled by sinc functions centered on N evenly spaced points distributed over L, then the direct application of equation (78) incorporates the implicit assumption that the surface magnetic field h (i.e. the current) is zero at all locations outside the region L. This enforces zero-current end boundary conditions, which may not match the physical situation: in practice the ends of the line may be attached to other lines or to electrical devices, and the precise calculation of the resulting electrical and magnetic fields would require the detailed application of Maxwell's equations to this region of the system.

For purposes of explanation, an approximate approach is taken which is in the spirit of transmission line theory. Initially each end of the line is short-circuited by applying a symmetry boundary condition, which yields non-zero end currents and zero end voltages. An impedance is then added to each end of the line, thus allowing general boundary conditions to be modelled; for example, a zero added impedance maintains the short circuit condition, whereas an infinite added impedance recovers the zero current condition. To consider initially the left hand end of the line ($x_3=0$), rather than assume the current is zero to the left of the first reference point $x_{3,1}$ the present approach assumes that the current is symmetric around this point, so that the electric field at some general point $x_{3,n}$ includes contributions from a non-zero current in the region $x_3<0$.

Imposing the symmetry condition as a constraint modifies the dielectric impedance matrix $Z_D$ to a matrix $Z_{DS}$, where $$Z_{DSnm}=(\tfrac{1}{2})\delta_{1n}\delta_{1m}Z_{Dnm}+[1-(\delta_{1n}+\delta_{1m})/2]\times[Z_{Dnm}+Z_D(2-n-m)], \quad (86)$$

and $\delta_{nm}$ is the Kronecker delta. In deriving equation (86) it has been noted that the mirror image of the point $x_{3,m}$ is at a distance $(m+n-2)\Delta x$ to the left of the point $x_{3,n}$; the additional electric field at the point $x_{3,n}$ arising from the current at the image point is accounted for by the appearance of the term $Z_D(2-n-m)$ in equation (86). Special consideration is needed when $n=1$ and/or $m=1$, since in these cases at least one of the two points lies on the axis of symmetry, and this introduces various factors of ½, which are accounted for by the presence of the Kronecker delta terms in equation (86). A similar modification must be applied to the impedance matrix $Z_C$ of the conducting material to yield a new matrix $Z_{CS}$.

As described above in the context of FIG. 5, the voltage matrix F which appears in equation (83) must also be modified to allow for the presence of the non-zero current in the region $x_3<0$, and this yields a matrix $F_S$ where $$F_{Snm}=F_{nm}+(1-\delta_{1m})F(2-n-m). \quad (87)$$

As mentioned previously, the application of the symmetry condition embodied equations (86) and (87) imposes a short circuit at the left hand end of the line. A more general boundary condition can be imposed be assuming that the current at the end of the line generates an additional electrical field; the approach taken here is to assume that a uniform surface electric field, $e_{gen}(x_3)$ say, is generated over a small region $-l \leq x_3 \leq l$, and that this field is proportional to the average current over this region, so that $$e_{gen}(x_3)=(R/l)[H(x_3+l)-H(x_3-l)]\{\int_{-l}^{l}h(x_3)dx_3/2l\}. \quad (88)$$

Here H is the Heavyside step function, and R is an impedance (a real value of R would represent a resistance). The average current over the small region can be written in terms of the generalized current vector in the form $$\int_{-l}^{l}h(x_3)dx_3/(2l)=c^Th, \quad (89)$$

where the vector c has the entries $$c_n=(2-\delta_{1n}-\delta_{nN})(2lk_s)^{-1}\times\{Si[k_s(x_{3,n}+l)]-Si[k_s(x_{3,n}-l)]\}, \quad (90)$$

with Si representing the sine integral function. With this notation, it follows that equation (88) can be enforced by adding the following matrix to $Z_{DS}$:

$$Z_R=Rcc^T. \quad (91)$$

A similar approach can be applied at the right hand end of the line $x_3=L$, leading to further modifications which are analogous to equations (86)-(91).

The units of the various terms described above can be summarized as follows: a surface electric field $e(x_3)$ has units of volts/m; a generalized electric field variable $e_n$ has units of volts; a surface magnetic field $h(x_3)$ and a generalized magnetic field variable $h_n$ each have units of amps; all impedance matrices Z have units of ohms; the impedance R has units of ohms and is equivalent to a simple end impedance that would be employed in a transmission line analysis based on the telegrapher's equations.

Response to Diffuse Field Excitation

Following equations (16)-(18) and incorporating modifications to allow for general end boundary conditions, the response of the transmission line to diffuse field excitation can be written as $$E[hh^{*T}] = \left(\frac{2\pi c}{\mu\omega^2}\right)E[|E|^2](Z_{DS}+Z_{CS}+Z_R)^{-1}Z_{DH}\times(Z_{DS}+Z_{CS}+Z_R)^{-T^*}, \quad (92)$$

where $E[|E|^2]$ is the mean square value of the modulus of the electric field vector of the incident wavefield at any point in the enclosing body surrounding the transmission line. For reference, it can be shown on the basis of equations (31)-(33) that the response of an infinite transmission line to diffuse field excitation is given by $$E[|h|^2] = \left(\frac{c}{\mu\omega^2}\right)E[|E|^2]\int_{-\infty}^{\infty}|\hat{Z}_D(k_3) + \hat{Z}_C(k_3)|^2 \hat{Z}_{DH}(k_3)\,dk_3. \quad (93)$$

Application of equations (92) and (93) will now be described below in the context of a number of different exemplary cases.

Numerical Example for a Single Wire Transmission Line

Figure 8:
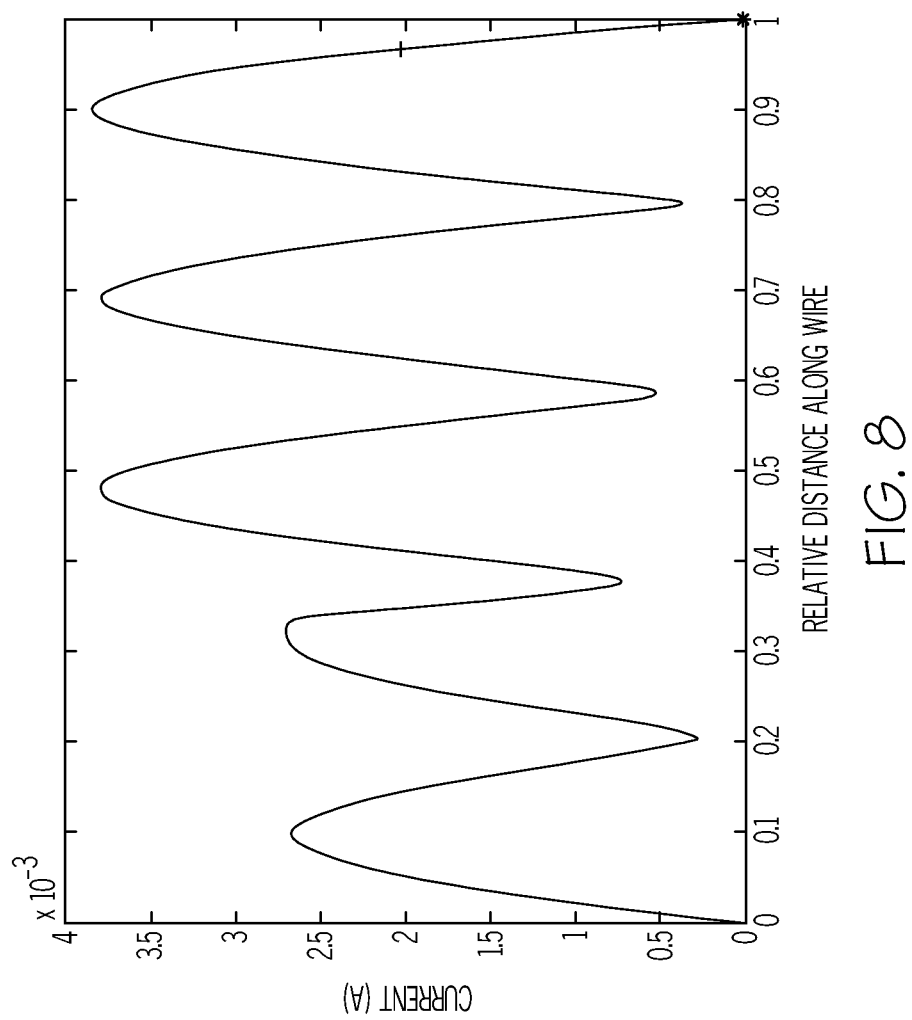
FIG. 8 is a graph of induced current with respect to distance along a conductive element suitable for presentation on the display device in the computing system of FIG. 2.

The first numerical example involves a single thin wire with radius to length ratio $a/L=10^{-4}$. FIG. 8 is a graphical representation of the induced current in the wire with respect to a distance (or position) along the wire in response to a unit voltage source with frequency $kL=15$ located at $x_3=L/3$, which has been represented by an axial electrical field of strength $1/(2l)$ applied uniformly over the region $|x_3-L/3| \le l$, with $l=10^{-3}$ L, and the dimensional values $L=0.5$ m, $\delta=\delta_c=8.854\times10^{-12}$ farad/m, $\mu=\mu_c=1.257\times10^{-6}$ henry/m and $\sigma_c=5.8\times10^7$ S/m. In this example, no special consideration has been given to the end boundary conditions, and thus, the default condition is zero current at each end of the wire, as illustrated in FIG. 8.

Figure 9:
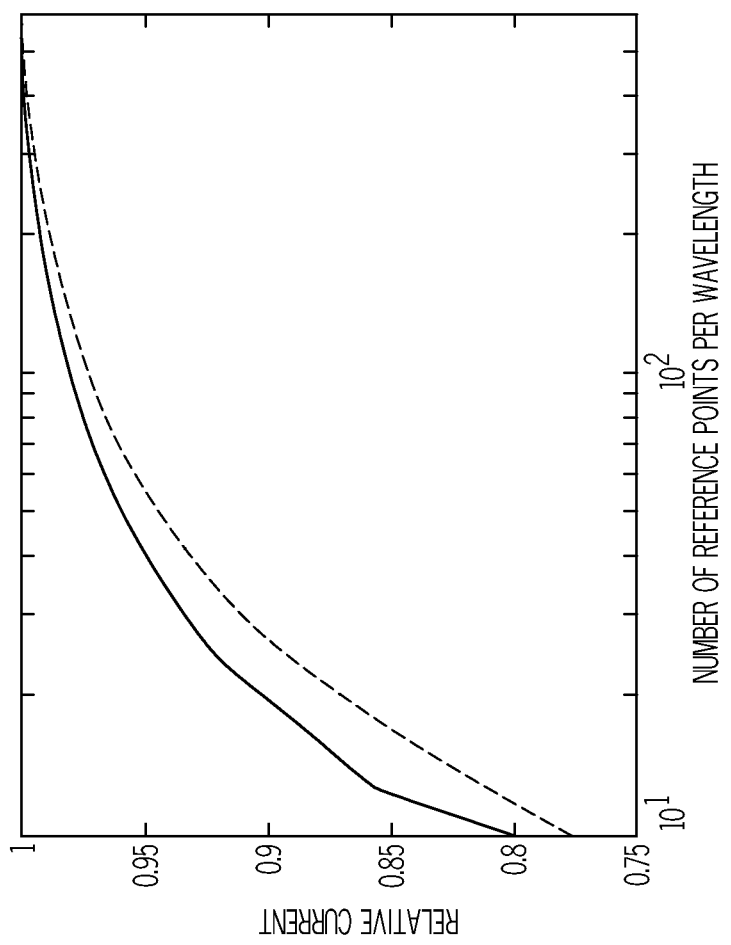
FIG. 9 is a graph depicting convergence results for a single wire transmission line corresponding to the excitation described in the context of FIG. 8.

FIG. 9 illustrates convergence results for a single wire transmission line showing the maximum current in the wire as a function of the number of reference points per electromagnetic wavelength $2\pi/k$. The relative current is defined as the maximum current divided by the result obtained when 600 reference points are used per wavelength, wherein the solid line represents the results for a unit voltage applied at $x_3=L/3$ and the dashed line represents the results for a diffuse field excitation with $kL=15$. It should be noted that the present method does not suffer from mesh density issues associated with the standard thin wire method of moments approach, in which the segment length must be at least eight to ten times the wire radius to avoid violating the assumptions inherent in the method, which places a limitation on the number of segments which can be employed, and hence the degree of convergence which can be attained. It can be seen from FIG. 9 that the use of 20 reference points per wavelength produces a maximum root mean square (rms) current which is 10% below that predicted by the use of 600 reference points per wavelength.

Turning now to the convergence results for the case in which the wire is excited by a homogeneous diffuse-electromagnetic field with $kL=15$, which is illustrated by the dashed line in FIG. 9, the incident diffuse field is fully characterized by the frequency of oscillation (or equivalently k) and the ensemble mean squared value of the modulus of the electric field, which has the same value at every point in the field. The ensemble average of the modulus squared current at any point on the wire can be computed from equation (92), and the results which follow concern the square root of this quantity, referred to here as the root mean square (rms) current, which varies along the wire. In FIG. 9 the maximum rms current in the wire is plotted against the number of reference points used in the numerical model. It can be seen that the convergence rate for the case of diffuse field excitation is slightly slower than that for a concentrated voltage source, which is illustrated by the solid line in FIG. 9.

Figure 10:
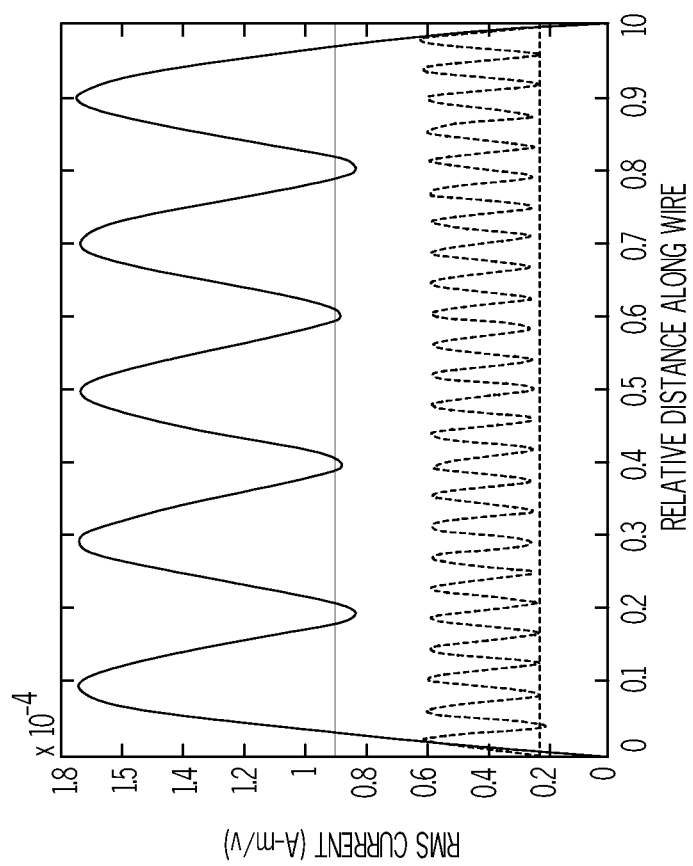
FIG. 10 is a graph of induced current with respect to distance along a conductive element in response to diffuse field excitation that is suitable for presentation on the display device in the computing system of FIG. 2 in conjunction with the induced field determination process of FIG. 3.
Figure 11:
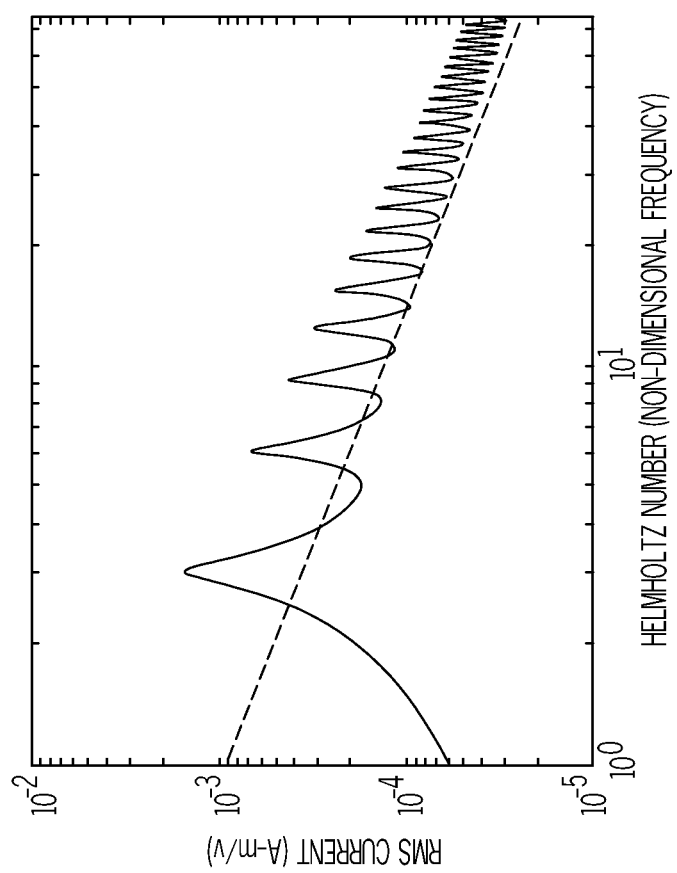
FIG. 11 is a graph of induced current as a function of frequency corresponding to the excitation described in the context of FIG. 10.

FIG. 10 depicts an exemplary graphical representation of the rms current scaled by the rms electrical field strength as a function of relative distance along the wire $x_3/L$ for diffuse field excitation, wherein the solid line represents an incident diffuse field with $kL=15$ (which corresponds to excitation at 1.43 GHz), the dashed line represents an incident diffuse field with $kL=75$ (which corresponds to excitation at 7.16 GHz), the solid horizontal line represents the response of an infinite wire with the incident diffuse field having $kL=15$ computed using equation (93), and the dashed horizontal line represents the response of an infinite wire with the incident diffuse field having $kL=15$. The response of the wire to electromagnetic excitation can be considered to consist of two components, a particular integral and a complementary function. In the present case the particular integral is the response of an infinite wire to diffuse field excitation, while the complementary function is the additional response needed to match the end boundary conditions. As illustrated, the complementary function tends to increase the rms current for the cases shown in FIG. 10. In general the combined response will depend upon the relative phase between the two components of the response, and this issue is illustrated in FIG. 11, which shows the spatial average of the rms current as a function of frequency; it can be seen that at some frequencies the response of an infinite wire exceeds that of the finite system. It will be appreciated that the graphical representation of the induced current depicted in FIG. 10 is one potential output that may be generated by the process 300 (e.g., task 310). For example, the user may provide to the processing system 204, via user input device 202, the parameters defining the incident electromagnetic wavefield 108 and the length of the conductive element 102, wherein the processing system 204 subsequently executes the processes or otherwise performs the equations described above to obtain the induced current as a function of the distance (or relative position) along the conductive element and generates a graphical representation of the induced current that is provided to or otherwise displayed on the display device 206.

Numerical Example for a Two Wire Transmission Line

Figure 12:
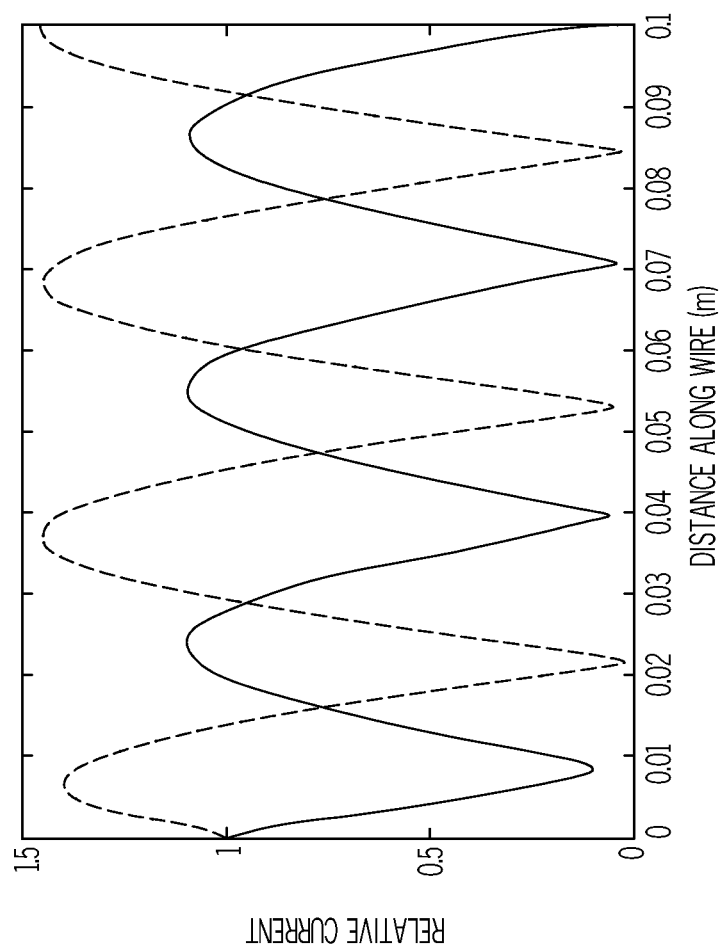
FIG. 12 is a graph of induced current with respect to distance along a conductive element illustrating the effect of varying the boundary conditions at one or more ends of the conductive element.
Figure 13:
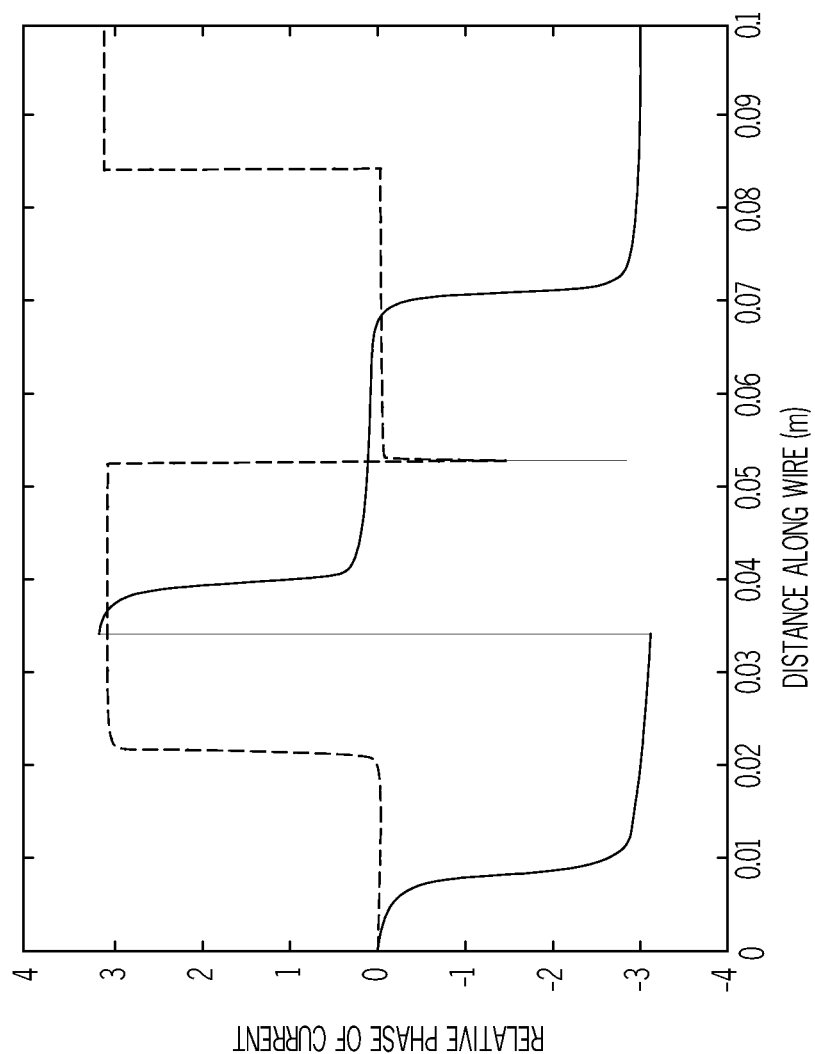
FIG. 13 is a graph of the phase of the induced currents depicted in FIG. 12 with respect to distance along the conductive element illustrating the effect of varying the boundary conditions at one or more ends of the conductive element.
Figure 14:
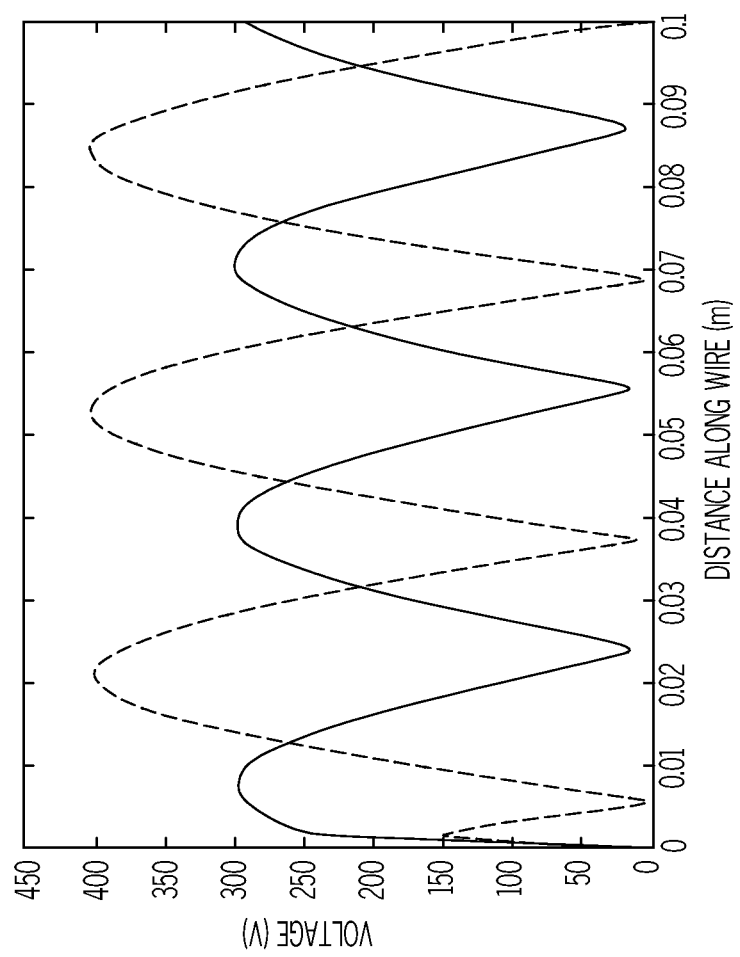
FIG. 14 is a graph of induced voltage with respect to distance along the conductive element illustrating the effect of varying the boundary conditions at one or more ends of the conductive element.

Referring now to FIGS. 12-14, the second numerical example concerns a two wire transmission line of length $L=0.1$ m, spacing $d=0.01$ m, and radius $a=1$ mm in response to a harmonic voltage applied at $x_3=0$ (e.g., the left hand end) for the frequency $kd=1$, which corresponds to 4.77 GHz. FIG. 12 is a graphical representation of the relative current induced in the wire as a function of the distance along the wire, where relative current is defined as the current at a particular location on the wire divided by the current at $x_3=0$. FIG. 13 is a graphical representation of the phase of the relative current as a function of distance along the wire, and FIG. 14 is a graphical representation of the voltage as a function of distance along the wire. In FIGS. 12-14, the solid line represents results for zero current at the right hand end. It will be appreciated that each of the graphical representations depicted in FIGS. 12-14 is a potential output that may be generated by the process 300 (e.g., task 310). The results illustrated in FIGS. 12-14 were obtained using the approaches described above based on equation (65). At the left hand end of the wire a symmetry boundary condition was applied to allow the current to be non-zero, as described above. The applied voltage was then modelled as an axial electrical field of strength $1/(4l)$ applied to each wire in opposite directions over the region $|x_3| \le l$, with $l=0.0175$ m. In contrast, no symmetry condition was applied at the right hand end of the wire, so that the default boundary condition of zero current was obtained. In considering the voltage distribution illustrated in FIG. 14, it should be noted that a symmetry condition on current leads to an anti-symmetry condition on voltage, and hence the voltage predicted precisely at the left hand end of the wire is zero, which is incorrect. This is not a significant problem however, since the voltage is predicted correctly over the remainder of the wire, and the voltage predicted very near to the left hand end is a close approximation to the true terminating value.

To further demonstrate the effect of the boundary conditions, results are shown in FIGS. 12-14 for the additional case in which the right hand end of the wire is short circuited, illustrated by the dashed line, which is achieved analytically by applying a symmetry boundary condition at that point. As would be expected, a non-zero current and a zero voltage are obtained at the right hand end of the wire for this case.

Figure 15:
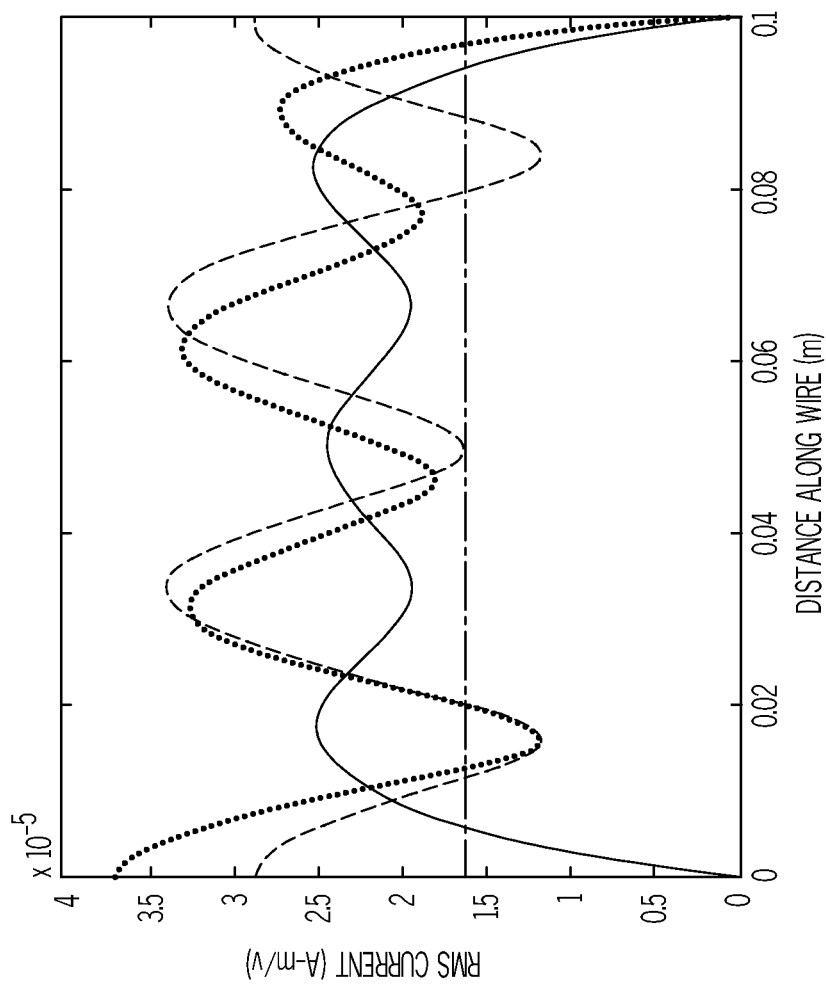
FIG. 15 is a graph of induced current with respect to distance along a conductive element in response to a diffuse field excitation that is suitable for presentation on the display device in the computing system of FIG. 2 in conjunction with the induced field determination process of FIG. 3.

FIG. 15 depicts a graphical representation of the rms transmission mode current (scaled by the rms electrical field strength) that is induced in the wire by a diffuse electromagnetic field as a function of distance along the wire for diffuse field excitation with kd=1. In FIG. 15, the solid line represents the boundary conditions of zero current at each end of the wire, the dashed line represents the boundary conditions of zero voltage (i.e., a short circuit) at each end of the wire, and the dotted line represents the boundary conditions of zero current at the right hand end of the wire and a short circuit at the left hand end. The results depicted in FIG. 15 are obtained by employing the transmission mode impedances, based on equations (65) and (69), in the response expression provided by equation (92). The dash-dot line in FIG. 15 illustrates the rms transmission mode current induced in an infinite transmission line, as given by equation (93). It can be seen that the maximum transmission mode current in the wire depends on the detailed boundary conditions, although the response of the infinite line, which can be computed very rapidly compared to the response of the finite line, yields a good first approximation of the general magnitude of the current; this is also the case for the previous example of a single wire, as evidenced by FIGS. 10-11.

Figure 16:
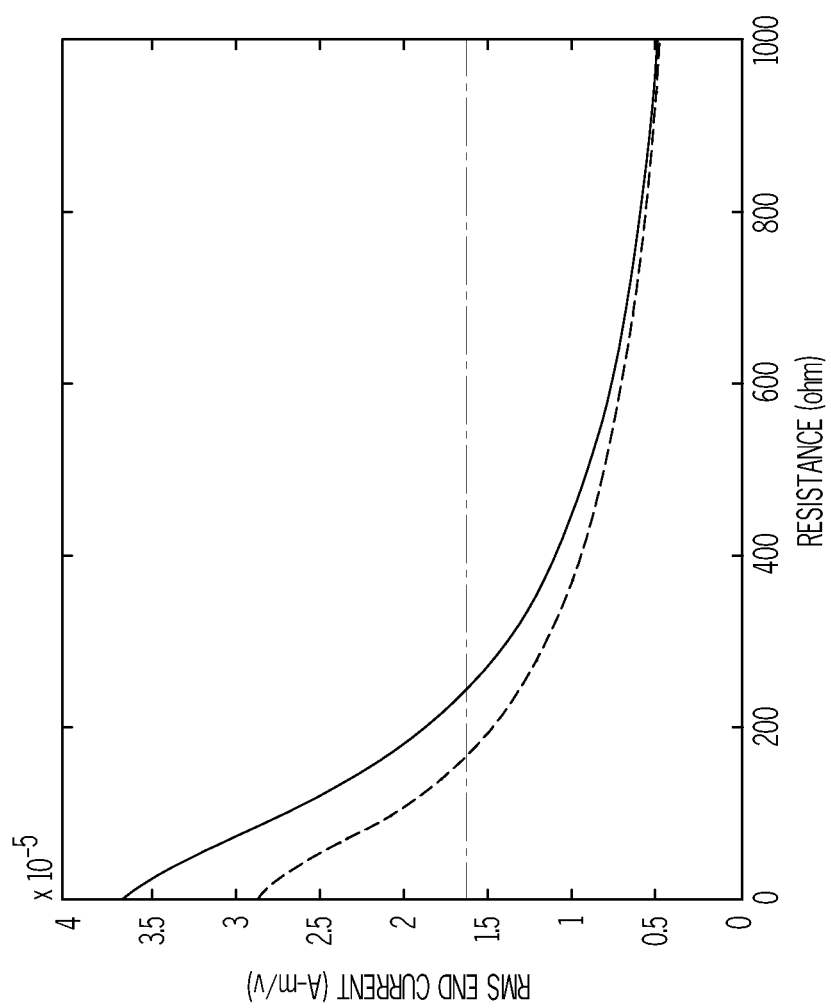
FIG. 16 is a graph of induced current with respect to a termination resistance in response to the diffuse field excitation described in the context of FIG. 15.

FIG. 16 illustrates the effect of adding a resistor to the left hand end of the transmission line, obtained via equation (91), for the two cases of a short circuit at the right hand end, illustrated by the dashed line, and a zero current at the right hand end, illustrated by the solid line, wherein the dash-dot line represents the corresponding result for a transmission line of infinite length obtained via equation (93). The rms current through the resistor is plotted against the value of the resistor R; for R=0 the line is short circuited, while for large R the current tends to zero. This example is indicative of the way in which the impedance of a device attached to the end of the wire can affect the current flow into the device.

In addition to the transmission mode current illustrated by FIGS. 15-16, diffuse field excitation of the two wire system can induce an antenna mode current. The complete current can be calculated by considering the full impedance matrix of the system, given by equation (59), rather than the reduced scalar impedance associated with the transmission mode, given by equation (65). The full impedance matrix in wavenumber space, obtained from equation (59), can be transformed to physical space by placing a grid of evenly spaced reference points along each wire, and assigning an independent generalized coordinate $h_n$ to each reference point. If there are N reference points on each wire then the model will have 2N degrees of freedom, and the associated 2N×2N impedance matrix can be computed by employing equation (25) in conjunction with the wavenumber space impedance matrix from equation (59). The diffuse field reciprocity relation can then be used to compute the response of the system via equation (92).

Referring now to FIG. 17, if equation (92) is used to compute the correlation matrix of the total current in the two wire system, then the rms transmission and antenna mode currents can be deduced: at a location $x_3$ the transmission mode current is defined as $[h_1(x_3)-h_2(x_3)]/2$ and the antenna mode current as $[h_1(x_3)+h_2(x_3)]/2$, where $h_1$ and $h_2$ are the currents in the two wires. FIG. 17 depicts a graphical representation of the rms current (scaled by the rms electrical field strength) as a function of distance along the wire for a two wire transmission line with a short circuit at each end for diffuse field excitation with kd=1. In FIG. 17, the solid line represents the total current, the dashed line represents the transmission mode current, and the dotted line represents the antenna mode current. As illustrated, the result for the transmission mode current is in agreement with that shown in FIG. 15, while the antenna mode current is greater than the transmission mode current. The maximum of total current in the wire has an rms value that is around twice the maximum rms transmission mode current. Clearly the presence of the antenna mode can significantly affect the current in the interior of the wire, although only the transmission mode will affect the current drawn at the terminations. The present example demonstrates that the diffuse field reciprocity principle can be employed to yield all components of the current induced in the system.

CONCLUSION

As described herein, in the context of electromagnetism, the diffuse field reciprocity principle states that the excitation applied to a system by a diffuse electromagnetic field can be expressed in terms of the surface electromagnetic impedance matrix of the system, as represented by equation (15). The surface electromagnetic impedance matrix of a wire system can be formulated in terms of exact solutions to Maxwell's equations in cylindrical coordinates; results in the frequency domain (or wavenumber space) have been presented above for one- and two wire systems respectively, and a numerical approach for expressing these results in the spatial domain has also been provided. By accommodating various boundary conditions at the ends of the wire, the subject matter described herein may be extended to models of various different wiring systems and cable networks.

One advantage of the subject matter described herein is that the diffuse field reciprocity principle allows the rms currents induced by a diffuse electromagnetic field to be computed in a straight forward and efficient way. In this regard, once the system impedance matrices have been calculated, predicting the response of the wire to diffuse field excitation is a relatively trivial computational step as compared to previous approaches, such as those requiring a full computation of the electromagnetic field in the surrounding enclosure. At the same time, the response computed by using the diffuse field reciprocity principle will be substantially identical to the result yielded by a "direct" calculation in which the diffuse electromagnetic field is represented as a summation of random plane waves (e.g., by calculating the excitation arising from individual plane waves and summing the response arising from each plane wave component), which requires a significant amount of computation time, since a sufficient number of waves with varying heading, azimuth, and polarization angle must be considered to produce an adequate representation of the diffuse field. Furthermore, the present approach immediately provides a statistically averaged result, whereas other approaches would require multiple randomized computations to generate an ensemble of results which can then be averaged to yield mean square values.

For purposes of explanation, the subject matter may be described herein in terms of functional and/or logical block components, and with reference to symbolic representations of operations, processing tasks, and functions that may be performed by various computing components or devices.

Such operations, tasks, and functions are sometimes referred to as being computer-executed, computerized, software-implemented, or computer-implemented. In this regard, it should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method comprising:
   executing one or more first computer instructions configured to predict a response of a conductive element to an electromagnetic wavefield incident to a surface of the conductive element, wherein executing the one or more first computer instructions comprises:
      executing one or more second computer instructions configured to determine an electromagnetic impedance associated with electromagnetic radiation at the surface of the conductive element in an infinite dielectric medium; and
      executing one or more third computer instructions configured to apply diffuse field reciprocity using the electromagnetic impedance to obtain a metric indicative of an induced field resulting from the electromagnetic wavefield incident to the surface of the conductive element;
   and
   executing one or more fourth computer instructions configured to display an output based on the metric on a display device;
   wherein:
      executing the one or more first computer instructions further comprises at least one of (i) executing one or more fifth computer instructions configured to determine an induced current metric based on the metric or (ii) executing one or more sixth computer instructions configured to determine a voltage recovery matrix for the conductive element and executing one or more seventh computer instructions configured to determine an induced voltage metric based on the voltage recovery matrix and the metric;
   when executing the one or more first computer instructions comprises executing the one or more fifth computer instructions:
      executing the one or more fourth computer instructions comprises executing one or more eight computer instruction configured to display a graphical representation of the induced current metric on the display device, the output comprising the graphical representation of the induced current metric;
      the induced current metric comprises an induced current as a function of position along the surface of the conductive element; and
      the graphical representation of the induced current metric comprises a graph of the induced current as the function of position along the surface of the conductive element;
   when executing the one or more first computer instructions comprises executing the one or more sixth computer instructions and the one or more seventh computer instructions;
      executing the one or more fourth computer instructions comprises executing one or more ninth computer instruction configured to display a graphical representation of the induced voltage metric on the display device, the output comprising the graphical representation of the induced voltage metric;
      the induced voltage metric comprises an induced voltage as a function of position along the surface of the conductive element; and
      the graphical representation of the induced voltage metric comprises a graph of the induced voltage as the function of position along the surface of the conductive element;
   and
   the one or more first computer instructions and the one or more fourth computer instructions are configured to run at one or more processors and configured to be stored at one or more non-transitory memory storage modules.

2. The method of claim 1, wherein:
the electromagnetic impedance represents a relationship between an electric field and a magnetic field at the surface of the conductive element in the infinite dielectric medium.

3. The method of claim 1, wherein:
executing the one or more third computer instructions comprises executing one or more tenth computer instructions configured to multiply a resistive part of the electromagnetic impedance by an energy metric associated with the electromagnetic wavefield incident to the surface of the conductive element.

4. The method of claim 1, wherein:
executing the one or more first computer instructions further comprises executing one or more tenth computer instructions configured to receive an incident wavefield metric based on an energy density of the electromagnetic wavefield incident to the surface of the conductive element; and
executing the one or more third computer instructions comprises executing one or more eleventh computer instructions configured to multiply the electromagnetic impedance by the incident wavefield metric.

5. The method of claim 1, wherein:
the metric comprises cross-spectrum of a blocked electric field arising from the electromagnetic wavefield incident to the surface of the conductive element.

6. The method of claim 1, wherein:
executing the one or more second computer instructions comprises executing one or more tenth computer instructions configured to determined an electromagnetic impedance matrix in wavenumber space.

7. The method of claim 6, wherein:
executing the one or more second computer instructions further comprises executing one or more eleventh computer instructions configured to transform the electromagnetic impedance matrix from the wavenumber space to a physical domain.

8. The method of claim 7, wherein:
executing the one or more eleventh computer instructions comprises executing one or more twelfth computer instructions configured to transform the electromagnetic impedance matrix from the wavenumber space to the physical domain with basis functions based on sinc function.

9. The method of claim 7, wherein:
executing the one or more second computer instructions further comprises executing one or more twelfth computer instructions configured to impose a boundary condition to the electromagnetic impedance in the physical domain to obtain a modified electromagnetic impedance matrix; and
executing the one or more third computer instructions comprises executing one or more thirteenth computer instructions configured to multiply the modified wavefield incident to the surface of the conductive element to obtain the metric.

10. The method of claim 6, wherein:
executing the one or more second computer instructions comprises executing one or more eleventh computer instructions configured to determine the electromagnetic impedance matrix in wavenumber space based on exact solutions to Maxwell's equations in cylindrical coordinates.

11. A non-transitory computer-readable medium having instructions stored thereon executable by a processing system to:
predict a response of a conductive element to an incident electromagnetic wavefield by:
determining a surface electromagnetic impedance matrix for the conductive element in an infinite dielectric medium based on physical dimensions of the conductive element and an excitation frequency for the incident electromagnetic wavefield;
determining with diffuse field reciprocity a metric indicative of an induced field in the conductive element resulting from the incident electromagnetic wavefield based at least in part on the surface electromagnetic impedance matrix and an energy metric for the incident electromagnetic wavefield;
and
at least one of:
determining an induced current metric based on the metric; or
determining a voltage recovery matrix for the conductive element, and determining an induced voltage metric based on the voltage recovery matrix and the metric;
and
display an output based on the metric on a display device coupled to the processing system;
wherein:
when the instructions are executable by the processing system to determine the induced current metric based on the metric, the instructions are executable by the processing system to display the output based on the metric on the display device coupled to the processing system by:
displaying a graphical representation of the induced current metric on the display device, the output comprising the graphical representation of the induced current metric, the induced current metric comprising an induced current as a function of position along the conductive element, and the graphical representation of the induced current metric comprising a graph of the induced current as a function of position along the conductive element;
and
when the instructions are executable by the processing system to determine the voltage recovery matrix for the conductive element and to determine the induced voltage metric based on the voltage recovery matrix and the metric, the instructions are executable by the processing system to display the output based on the metric on the display device coupled to the processing system by:
displaying a graphical representation of the induced voltage metric on the display device, the output comprising the graphical representation of the induced voltage metric, the induced voltage metric comprising an induced voltage as a function of position along the conductive element, and the graphical representation of the induced voltage metric comprising a graph of the induced voltage as the function of position along the conductive element.

12. The non-transitory computer-readable medium of claim 11, wherein the instructions are executable by the processing system to:
predict the response of the conductive element to the incident electromagnetic wavefield further by:
obtaining the physical dimensions for the conductive element via a user input device coupled to the processing system; and
obtaining excitation parameters for the incident electromagnetic wavefield via the user input device, the excitation parameters including the excitation frequency and the energy metric.

13. The non-transitory computer-readable medium of claim 12, wherein the instructions are executable by the processing system to:
display graphical user interface elements adapted to receive the physical dimensions and the excitation parameters on the display device.

14. The non-transitory computer-readable medium of claim 11, wherein the instructions are executable by the processing system to:
determine the metric by applying the diffuse field reciprocity using the surface electromagnetic impedance matrix and the energy metric to obtain an induced magnetic field metric.

15. A method comprising:
executing one or more first computer instructions configured to model an effect of an electromagnetic wavefield incident on a conductive element, the executing the one or more first computer instructions comprising:
executing one or more second computer instructions configured to obtain, via a user input device, physical dimensions of the conductive element;
executing one or more third computer instructions configured to obtain, via the user input device, an excitation frequency and an energy metric for a diffuse electromagnetic wavefield incident on the conductive element;
executing one or more fourth computer instructions configured to determine a surface electromagnetic impedance matrix for the conductive element in an infinite dielectric medium based on the excitation frequency and the physical dimensions of the conductive element;

executing one or more fifth computer instructions configured to apply diffuse field reciprocity using the surface electromagnetic impedance matrix and the energy metric for the diffuse electromagnetic wavefield to obtain a metric indicative of an induced field resulting from the diffuse electromagnetic wavefield;

at least one of:

executing one or more sixth computer instructions configured to determine an induced current metric based on the metric, or executing one or more seventh computer instructions configured to determine a voltage recovery matrix for the conductive element, and executing one or more eight computer instructions configured to determine an induced voltage metric based on the voltage recovery matrix and the metric;

and executing one or more ninth computer instructions configured to display an output based on the display device;

wherein:

when executing the one or more first computer instructions comprises executing the one or more sixth computer instructions:

executing the one or more ninth computer instructions comprises executing one or more tenth computer instruction configured to display a graphical representation of the induced current metric on the display device, the output comprising the graphical representation of the induced current metric;

the induced current metric comprises an induced current as a function of position along the conductive element; and the graphical representation of the induced current metric comprises a graph of the induced current as the function of position along the conductive element:

when executing the one or more first computer instructions comprises executing the one or more seventh computer instructions and the one or more eight computer instructions:

executing the one or more ninth computer instructions comprises executing one or more eleventh computer instruction configured to display a graphical representation of the induced voltage metric on the display device, the output comprising the graphical representation of the induced voltage metric;

the induced voltage metric comprises an induced voltage as a function of position along the conductive element; and the graphical representation of the induced voltage metric comprises a graph of the induced voltage as the function of position along the conductive element:

the one or more first computer instructions are configured to run at one or more processors and configured to be stored at one or more non-transitory memory storage modules.

16. A computing system comprising:

a user input device;

a display device; and a processing system coupled to the user input device and the display device to:

obtain, via the user input device, physical dimensions of a conductive element;

obtain, via the user input device, an excitation frequency and an energy metric for an electromagnetic wavefield incident on the conductive element;

determine a surface electromagnetic impedance matrix for the conductive element in an infinite dielectric medium based on the excitation frequency and the physical dimensions of the conductive element;

apply diffuse field reciprocity using the surface electromagnetic impedance matrix and the energy metric for the electromagnetic wavefield to obtain a metric indicative of an induced field resulting from the electromagnetic wavefield;

at least one of:

determine an induced current metric based on the metric; or determine a voltage recovery matrix for the conductive element, and determine an induced voltage metric based on the voltage recovery matrix and the metric;

and display an output based on the metric on the display device;

wherein:

when the processing system is configured to determine the induced current metric based on the metric, the processing system is further configured to display the output based on the metric on the display device by:

displaying a graphical representation of the induced current metric on the display device, the output comprising the graphical representation of the induced current metric, the induced current metric comprising an induced current as a function of position along the conductive element, and the graphical representation of the induced current metric comprising a graph of the induced current as a function of position along the conductive element;

and when the processing system is configured to determine the voltage recovery matrix for the conductive element and to determine the induced voltage metric based on the voltage recovery matrix and the metric, the processing system is further configured to display the output based on the metric on the display device by:

displaying a graphical representation of the induced voltage metric on the display device, the output comprising the graphical representation of the induced voltage metric, the induced voltage metric comprising an induced voltage as a function of position along the conductive element, and the graphical representation of the induced voltage metric comprising a graph of the induced voltage as the function of position along the conductive element.

* * * * *